US008785159B2

(12) United States Patent
Linger et al.

(10) Patent No.: US 8,785,159 B2
(45) Date of Patent: Jul. 22, 2014

(54) EXTRACELLULAR SECRETION OF RECOMBINANT PROTEINS

(75) Inventors: Jeffrey G. Linger, Dever, CO (US); Aldis Darzins, Highlands Ranch, CO (US)

(73) Assignee: Alliance for Sustainable Energy, LLC, Golden, CO (US)

( * ) Notice: Subject to any disclaimer, the term of this patent is extended or adjusted under 35 U.S.C. 154(b) by 457 days.

(21) Appl. No.: 12/950,442

(22) Filed: Nov. 19, 2010

(65) Prior Publication Data

US 2011/0124046 A1 May 26, 2011

Related U.S. Application Data

(60) Provisional application No. 61/264,391, filed on Nov. 25, 2009.

(51) Int. Cl.
| | | |
|---|---|---|
| C12P 19/14 | (2006.01) | |
| C12N 15/00 | (2006.01) | |
| C12N 5/10 | (2006.01) | |
| C12N 1/20 | (2006.01) | |
| C12N 1/00 | (2006.01) | |
| C12N 1/12 | (2006.01) | |
| C12P 21/06 | (2006.01) | |
| C12P 21/04 | (2006.01) | |
| C12N 9/42 | (2006.01) | |

(52) U.S. Cl.
USPC .......... 435/99; 435/320.1; 435/325; 435/419; 435/252.3; 435/254.11; 435/257.2; 435/69.1; 435/69.7; 435/209

(58) Field of Classification Search
None
See application file for complete search history.

(56) References Cited

U.S. PATENT DOCUMENTS

| | | | |
|---|---|---|---|
| 4,952,501 A | | 8/1990 | Jasin et al. |
| 5,137,819 A | * | 8/1992 | Kilburn et al. ............ 435/179 |
| 5,514,583 A | | 5/1996 | Picataggio et al. |
| 5,536,655 A | | 7/1996 | Thomas et al. |
| 5,843,760 A | | 12/1998 | Zhang et al. |
| 5,919,654 A | | 7/1999 | Hama et al. |
| 6,566,107 B1 | | 5/2003 | Zhang |
| 7,059,993 B2 | | 6/2006 | Ding et al. |
| 7,223,575 B2 | | 5/2007 | Zhang et al. |

OTHER PUBLICATIONS

Linger et al., "Heterologous Expression and Extracellular Secretion of Cellulolytic Enzymes by *Zymomonas mobilis*", Appl. Environ. Microbiol. 76:6360-6369, 2010.*
Linger et al., "Heterologous expression of multiple cellulolytic enzymes in *Zymomonas mobilis*", 31st Symposium on Biotechnology for Fuels and Chemicals, San Francisco, CA, May 2009.*
UniProtKB Accession No. P14924, Nov. 24, 2009, 2 pages.*
GenPept Accession No. NC_006526, Apr. 25, 2009, 2 pages.*
KEGG Accession No. ZMO0130, Apr. 6, 2011, 1 page.*
Dictionary definition of "derive", Cambridge American English Dictionary at dictionary.cambridge.org, last viewed on Aug. 9, 2012, 1 page.*
Juengst, E. BMJ 326:1410-1411,2003.*
Arfman, et al., "Use of the tac Promoter and lacIq for the Controlled Expression of *Zymomonas mobilis* Fermentative Genes in *Escherichia coli* and *Zymomonas mobilis*", Journal of Bacteriology, Nov. 1992, vol. 174, No. 22, pp. 7370-7378.
Baker, et al., "A New Thermostable Endoglucanase, *Acidothermus cellulolyticus* E1: Synergism with *Trichoderma reesei* CBH I and Comparison to *Thermomonospora fusca* E5", Applied Biochemistry and Biotechnology, 1994, vol. 45-46, pp. 245-256.
Brestic-Goachet, et al., "Transfer and expression of a *Bacillus licheniformis* α-amylase gene in *Zymomonas mobilis*", Archives of Microbiology, 1990, vol. 153, No. 3, pp. 219-225.
Brestic-Goachet, et al., "Transfer and Expression of an *Erwinia chrysanthemi* Cellulase Gene in *Zymomonas mobilis*", Journal of General Microbiology, 1989, vol. 135, No. 4, pp. 893-902.
Galbe, et al., "Pretreatment of lignocellulosic materials for efficient bioethanol production", Advances in Biochemical Engineering/Biotechnology, vol. 108, pp. 41-65, 2007.
Goeddel, "Systems for Heterologous Gene Expression", Methods in Enzymology, 1990, vol. 185, pp. 3-7.
Kubo, et al., "Location of a Region of the Muscarinic Acetylcholine Receptor Involved in Selective Effector Coupling", FEBS Letters, Dec. 5, 1988, vol. 241, Nos. 1-2), pp. 119-125.
Lee, et al., "The Bacterial Twin-Arginine Translocation Pathway", Annual Review of Microbiology, 2006, vol. 60, pp. 373-395.
Pond, et al., "Cloning, Sequencing, and Characterization of the Principal Acid Phosphatase, the phoC+ Product *Zymomonas mobilis*", Journal of Bacteriology, Feb. 1989, vol. 171, No. 2, pp. 767-774.
Senthilkumar, et al., "Characterization of Multiple Promoters and Transcript Stability in the sacB-sacC Gene Cluster in *Zymomonas mobilis*", Archives of Microbiology, 2009, vol. 191, No. 6, pp. 529-541.
Taylor, et al., "Complete Cellulase System in the Marine Bacterium *Saccharophagus degradans* Strain 2-40T", Journal of Bacteriology, Jun. 2006, vol. 188, No. 11, pp. 3849-3861.
Yanase, et al., "Ethanol Production from Cellulosic Materials by Genetically Engineered *Zymomonas mobilis*", Biotechnology Letters, 2005, vol. 27, pp. 259-263.
Zhang, et al., "Metabolic Engineering of a Pentose Metabolism Pathway in Ethanologenic *Zymomonas mobilis*", Science, Jan. 13, 1990, vol. 267, pp. 240-243.

* cited by examiner

*Primary Examiner* — David J Steadman
(74) *Attorney, Agent, or Firm* — John C. Stolpa

(57) ABSTRACT

Nucleic acids encoding secretion signals, expression vectors containing the nucleic acids, and host cells containing the expression vectors are disclosed. Also disclosed are polypeptides that contain the secretion signals and methods of producing polypeptides, including methods of directing the extracellular secretion of the polypeptides. Exemplary embodiments include cellulase proteins fused to secretion signals, methods to produce and isolate these polypeptides, and methods to degrade lignocellulosic biomass.

18 Claims, 7 Drawing Sheets

Figure 1

| Plasmid | Schematic | Parent vector |
|---|---|---|
| pZB188 | | N/A |
| pFLAG-CTC | | N/A |
| pJL100 | Zm pSap | pZB188 |
| pJL101 | pTac – Gh12 (AAs 1-274) | pFlag-CTC |
| pJL103 | pTac – E1 (AAs 42-404) | pFlag-CTC |
| pJL108 | pTac – E1 (AAs 42-404) | pZB188 |
| pJL110 | Zm-S & pptc – E1 (AAs 42-404) – Zm-pdc 3' region | pZB188 |
| p25143 | pTac – E1-c/o (AAs 42-404) | pZB188 |
| p25144 | pTac – Gh12-c/o (AAs 1-274) | pZB188 |
| pJL111 | pTac – Zm130 – E1-c/o (AAs 42-404) | p25143 |
| pJL112 | pTac – Zm331 – E1-c/o (AAs 42-404) | p25143 |
| pJL113 | pTac – Zm130 – Gh12-c/o (AAs 1-274) | p25143 |

SEQUENCE LISTING

```
<160> NUMBER OF SEQ ID NOS: 22

<210> SEQ ID NO 1
<211> LENGTH: 87
<212> TYPE: DNA
<213> ORGANISM: Zymomonas mobilis
<220> FEATURE:
<221> NAME/KEY: CDS
<222> LOCATION: (1)..(87)

<400> SEQUENCE: 1 atg ata aaa gtc ccg cgg ttc atc tgt atg atc gcg ctt aca tcc agc      48
Met Ile Lys Val Pro Arg Phe Ile Cys Met Ile Ala Leu Thr Ser Ser
1               5                   10                  15 gtt ctg gca agc ggc ctt tct caa agc gtt tca gct cat                  87
Val Leu Ala Ser Gly Leu Ser Gln Ser Val Ser Ala His
            20                  25

<210> SEQ ID NO 2
<211> LENGTH: 29
<212> TYPE: PRT
<213> ORGANISM: Zymomonas mobilis

<400> SEQUENCE: 2

Met Ile Lys Val Pro Arg Phe Ile Cys Met Ile Ala Leu Thr Ser Ser
1               5                   10                  15

Val Leu Ala Ser Gly Leu Ser Gln Ser Val Ser Ala His
            20                  25
```

```
<210> SEQ ID NO 3
<211> LENGTH: 90
<212> TYPE: DNA
<213> ORGANISM: Zymomonas mobilis
<220> FEATURE:
<221> NAME/KEY: CDS
<222> LOCATION: (1)..(90)

<400> SEQUENCE: 3 atg aaa aga aag ctt ggt cgt cgc cag tta tta act ggc ttt gtt gcc      48
Met Lys Arg Lys Leu Gly Arg Arg Gln Leu Leu Thr Gly Phe Val Ala
1               5                   10                  15 ctt ggc ggt atg gcg att aca gct ggt aag gcg cag gct tct              90
Leu Gly Gly Met Ala Ile Thr Ala Gly Lys Ala Gln Ala Ser
            20                  25                  30

<210> SEQ ID NO 4
<211> LENGTH: 30
<212> TYPE: PRT
<213> ORGANISM: Zymomonas mobilis

<400> SEQUENCE: 4

Met Lys Arg Lys Leu Gly Arg Arg Gln Leu Leu Thr Gly Phe Val Ala
1               5                   10                  15

Leu Gly Gly Met Ala Ile Thr Ala Gly Lys Ala Gln Ala Ser
            20                  25                  30

<210> SEQ ID NO 5
<211> LENGTH: 1233
<212> TYPE: DNA
<213> ORGANISM: Artificial Sequence
<220> FEATURE:
<223> OTHER INFORMATION: Synthetic fusion sequence
<220> FEATURE:
<221> NAME/KEY: CDS
<222> LOCATION: (1)..(1233)

<400> SEQUENCE: 5 atg ata aaa gtc ccg cgg ttc atc tgt atg atc gcg ctt aca tcc agc      48
Met Ile Lys Val Pro Arg Phe Ile Cys Met Ile Ala Leu Thr Ser Ser
1               5                   10                  15 gtt ctg gca agc ggc ctt tct caa agc gtt tca gct cat gcc gga ggg      96
Val Leu Ala Ser Gly Leu Ser Gln Ser Val Ser Ala His Ala Gly Gly
            20                  25                  30 ggt tat tgg cat act tct ggg aga gaa att ttg gac gcg aat aac gtt     144
Gly Tyr Trp His Thr Ser Gly Arg Glu Ile Leu Asp Ala Asn Asn Val
        35                  40                  45 ccg gtc cgc att gct ggc atc aat tgg ttt ggt ttt gaa acg tgt aac     192
Pro Val Arg Ile Ala Gly Ile Asn Trp Phe Gly Phe Glu Thr Cys Asn
    50                  55                  60 tat gtg gtg cat gga ctg tgg tca cgt gac tat cgg tcg atg tta gac     240
Tyr Val Val His Gly Leu Trp Ser Arg Asp Tyr Arg Ser Met Leu Asp
65                  70                  75                  80 cag atc aaa agc tta ggc tat aat acc att cgt ctg cct tat agc gac     288
Gln Ile Lys Ser Leu Gly Tyr Asn Thr Ile Arg Leu Pro Tyr Ser Asp
                85                  90                  95 gat att ttg aaa ccc ggt acc atg ccc aat agc ata aac ttt tac caa     336
Asp Ile Leu Lys Pro Gly Thr Met Pro Asn Ser Ile Asn Phe Tyr Gln
            100                 105                 110 atg aat caa gat ttg cag ggt tta acg agt ctt caa gtt atg gat aaa     384
Met Asn Gln Asp Leu Gln Gly Leu Thr Ser Leu Gln Val Met Asp Lys
        115                 120                 125
```

```
att gtt gca tat gct ggg cag att ggt ctg cgt atc att ttg gat cgg      432
Ile Val Ala Tyr Ala Gly Gln Ile Gly Leu Arg Ile Ile Leu Asp Arg
130                 135                 140 cat cgt cct gat tgc tcc ggg cag tct gct ctt tgg tac acc tcg tcc      480
His Arg Pro Asp Cys Ser Gly Gln Ser Ala Leu Trp Tyr Thr Ser Ser
145                 150                 155                 160 gtc agt gaa gct acc tgg att tca gat tta cag gcg ttg gct cag cgg      528
Val Ser Glu Ala Thr Trp Ile Ser Asp Leu Gln Ala Leu Ala Gln Arg
                165                 170                 175 tat aaa ggt aat cct act gtt gtt ggt ttt gat ttg cat aac gaa ccg      576
Tyr Lys Gly Asn Pro Thr Val Val Gly Phe Asp Leu His Asn Glu Pro
            180                 185                 190 cat gac ccg gct tgc tgg ggt tgt gga gat cct agc ata gat tgg cgc      624
His Asp Pro Ala Cys Trp Gly Cys Gly Asp Pro Ser Ile Asp Trp Arg
        195                 200                 205 ttg gcc gcc gaa cgg gcc gga aac gct gtc ctt tca gta aat ccg aat      672
Leu Ala Ala Glu Arg Ala Gly Asn Ala Val Leu Ser Val Asn Pro Asn
210                 215                 220 ttg ttg att ttt gtt gag ggt gtt caa tca tat aac ggg gat agc tat      720
Leu Leu Ile Phe Val Glu Gly Val Gln Ser Tyr Asn Gly Asp Ser Tyr
225                 230                 235                 240 tgg tgg gga ggg aat ctg caa gga gca ggt caa tat ccc gtt gtc ctg      768
Trp Trp Gly Gly Asn Leu Gln Gly Ala Gly Gln Tyr Pro Val Val Leu
                245                 250                 255 aat gtc cct aac cgt ttg gtt tat agc gcc cat gat tat gca acg tcg      816
Asn Val Pro Asn Arg Leu Val Tyr Ser Ala His Asp Tyr Ala Thr Ser
            260                 265                 270 gtt tat ccc caa acc tgg ttt agc gat cca aca ttt cct aat aac atg      864
Val Tyr Pro Gln Thr Trp Phe Ser Asp Pro Thr Phe Pro Asn Asn Met
        275                 280                 285 ccc ggc att tgg aat aag aac tgg gga tat ctt ttt aat caa aat att      912
Pro Gly Ile Trp Asn Lys Asn Trp Gly Tyr Leu Phe Asn Gln Asn Ile
290                 295                 300 gcc ccc gtt tgg ctt ggc gaa ttt ggt act acc ttg cag tct acc acc      960
Ala Pro Val Trp Leu Gly Glu Phe Gly Thr Thr Leu Gln Ser Thr Thr
305                 310                 315                 320 gat cag acc tgg ctt aaa acc tta gtt cag tat tta cgg cct acg gcc     1008
Asp Gln Thr Trp Leu Lys Thr Leu Val Gln Tyr Leu Arg Pro Thr Ala
                325                 330                 335 caa tat ggg gct gat agt ttc cag tgg aca ttt tgg tcc tgg aat ccg     1056
Gln Tyr Gly Ala Asp Ser Phe Gln Trp Thr Phe Trp Ser Trp Asn Pro
            340                 345                 350 gac agt ggc gat acc ggc ggc atc ttg aag gac gac tgg cag aca gtt     1104
Asp Ser Gly Asp Thr Gly Gly Ile Leu Lys Asp Asp Trp Gln Thr Val
        355                 360                 365 gat acc gta aaa gat ggt tat ctt gcc ccg atc aag tct tcc atc ttc     1152
Asp Thr Val Lys Asp Gly Tyr Leu Ala Pro Ile Lys Ser Ser Ile Phe
370                 375                 380 gac cca gtg ggc gca tct gcc tcc cct tcc tcc caa ccc tcc cct agt     1200
Asp Pro Val Gly Ala Ser Ala Ser Pro Ser Ser Gln Pro Ser Pro Ser
385                 390                 395                 400 gtg agc cca tca ccc agt ccc agt cca agc taa                          1233
Val Ser Pro Ser Pro Ser Pro Ser Pro Ser
                405                 410

<210> SEQ ID NO 6
<211> LENGTH: 410
<212> TYPE: PRT
<213> ORGANISM: Artificial Sequence
<220> FEATURE:
<223> OTHER INFORMATION: Synthetic Construct
```

<400> SEQUENCE: 6

```
Met Ile Lys Val Pro Arg Phe Ile Cys Met Ile Ala Leu Thr Ser Ser
1               5                   10                  15

Val Leu Ala Ser Gly Leu Ser Gln Ser Val Ser Ala His Ala Gly Gly
            20                  25                  30

Gly Tyr Trp His Thr Ser Gly Arg Glu Ile Leu Asp Ala Asn Asn Val
            35                  40                  45

Pro Val Arg Ile Ala Gly Ile Asn Trp Phe Gly Phe Glu Thr Cys Asn
        50                  55                  60

Tyr Val Val His Gly Leu Trp Ser Arg Asp Tyr Arg Ser Met Leu Asp
65                  70                  75                  80

Gln Ile Lys Ser Leu Gly Tyr Asn Thr Ile Arg Leu Pro Tyr Ser Asp
            85                  90                  95

Asp Ile Leu Lys Pro Gly Thr Met Pro Asn Ser Ile Asn Phe Tyr Gln
            100                 105                 110

Met Asn Gln Asp Leu Gln Gly Leu Thr Ser Leu Gln Val Met Asp Lys
        115                 120                 125

Ile Val Ala Tyr Ala Gly Gln Ile Gly Leu Arg Ile Ile Leu Asp Arg
130                 135                 140

His Arg Pro Asp Cys Ser Gly Gln Ser Ala Leu Trp Tyr Thr Ser Ser
145                 150                 155                 160

Val Ser Glu Ala Thr Trp Ile Ser Asp Leu Gln Ala Leu Ala Gln Arg
            165                 170                 175

Tyr Lys Gly Asn Pro Thr Val Val Gly Phe Asp Leu His Asn Glu Pro
        180                 185                 190

His Asp Pro Ala Cys Trp Gly Cys Gly Asp Pro Ser Ile Asp Trp Arg
    195                 200                 205

Leu Ala Ala Glu Arg Ala Gly Asn Ala Val Leu Ser Val Asn Pro Asn
        210                 215                 220

Leu Leu Ile Phe Val Glu Gly Val Gln Ser Tyr Asn Gly Asp Ser Tyr
225                 230                 235                 240

Trp Trp Gly Gly Asn Leu Gln Gly Ala Gly Gln Tyr Pro Val Val Leu
            245                 250                 255

Asn Val Pro Asn Arg Leu Val Tyr Ser Ala His Asp Tyr Ala Thr Ser
            260                 265                 270

Val Tyr Pro Gln Thr Trp Phe Ser Asp Pro Thr Phe Pro Asn Asn Met
        275                 280                 285

Pro Gly Ile Trp Asn Lys Asn Trp Gly Tyr Leu Phe Asn Gln Asn Ile
290                 295                 300

Ala Pro Val Trp Leu Gly Glu Phe Gly Thr Thr Leu Gln Ser Thr Thr
305                 310                 315                 320

Asp Gln Thr Trp Leu Lys Thr Leu Val Gln Tyr Leu Arg Pro Thr Ala
            325                 330                 335

Gln Tyr Gly Ala Asp Ser Phe Gln Trp Thr Phe Trp Ser Trp Asn Pro
        340                 345                 350

Asp Ser Gly Asp Thr Gly Gly Ile Leu Lys Asp Asp Trp Gln Thr Val
    355                 360                 365

Asp Thr Val Lys Asp Gly Tyr Leu Ala Pro Ile Lys Ser Ser Ile Phe
370                 375                 380

Asp Pro Val Gly Ala Ser Ala Ser Pro Ser Ser Gln Pro Ser Pro Ser
385                 390                 395                 400

Val Ser Pro Ser Pro Ser Pro Ser
            405                 410
```

-continued

```
<210> SEQ ID NO 7
<211> LENGTH: 1236
<212> TYPE: DNA
<213> ORGANISM: Artificial Sequence
<220> FEATURE:
<223> OTHER INFORMATION: Synthetic fusion sequence
<220> FEATURE:
<221> NAME/KEY: CDS
<222> LOCATION: (1)..(1236)

<400> SEQUENCE: 7
```

| atg | aaa | aga | aag | ctt | ggt | cgt | cgc | cag | tta | tta | act | ggc | ttt | gtt | gcc | 48 |
|---|---|---|---|---|---|---|---|---|---|---|---|---|---|---|---|---|
| Met | Lys | Arg | Lys | Leu | Gly | Arg | Arg | Gln | Leu | Leu | Thr | Gly | Phe | Val | Ala | |
| 1 | | | | 5 | | | | | 10 | | | | | 15 | | |

| ctt | ggc | ggt | atg | gcg | att | aca | gct | ggt | aag | gcg | cag | gct | tct | gcc | gga | 96 |
|---|---|---|---|---|---|---|---|---|---|---|---|---|---|---|---|---|
| Leu | Gly | Gly | Met | Ala | Ile | Thr | Ala | Gly | Lys | Ala | Gln | Ala | Ser | Ala | Gly | |
| | | | 20 | | | | | 25 | | | | | 30 | | | |

| ggg | ggt | tat | tgg | cat | act | tct | ggg | aga | gaa | att | ttg | gac | gcg | aat | aac | 144 |
|---|---|---|---|---|---|---|---|---|---|---|---|---|---|---|---|---|
| Gly | Gly | Tyr | Trp | His | Thr | Ser | Gly | Arg | Glu | Ile | Leu | Asp | Ala | Asn | Asn | |
| | | 35 | | | | | 40 | | | | | 45 | | | | |

| gtt | ccg | gtc | cgc | att | gct | ggc | atc | aat | tgg | ttt | ggt | ttt | gaa | acg | tgt | 192 |
|---|---|---|---|---|---|---|---|---|---|---|---|---|---|---|---|---|
| Val | Pro | Val | Arg | Ile | Ala | Gly | Ile | Asn | Trp | Phe | Gly | Phe | Glu | Thr | Cys | |
| | 50 | | | | | 55 | | | | | 60 | | | | | |

| aac | tat | gtg | gtt | cat | gga | ctg | tgg | tca | cgt | gac | tat | cgg | tcg | atg | tta | 240 |
|---|---|---|---|---|---|---|---|---|---|---|---|---|---|---|---|---|
| Asn | Tyr | Val | Val | His | Gly | Leu | Trp | Ser | Arg | Asp | Tyr | Arg | Ser | Met | Leu | |
| 65 | | | | | 70 | | | | | 75 | | | | | 80 | |

| gac | cag | atc | aaa | agc | tta | ggc | tat | aat | acc | att | cgt | ctg | cct | tat | agc | 288 |
|---|---|---|---|---|---|---|---|---|---|---|---|---|---|---|---|---|
| Asp | Gln | Ile | Lys | Ser | Leu | Gly | Tyr | Asn | Thr | Ile | Arg | Leu | Pro | Tyr | Ser | |
| | | | | 85 | | | | | 90 | | | | | 95 | | |

| gac | gat | att | ttg | aaa | ccc | ggt | acc | atg | ccc | aat | agc | ata | aac | ttt | tac | 336 |
|---|---|---|---|---|---|---|---|---|---|---|---|---|---|---|---|---|
| Asp | Asp | Ile | Leu | Lys | Pro | Gly | Thr | Met | Pro | Asn | Ser | Ile | Asn | Phe | Tyr | |
| | | | 100 | | | | | 105 | | | | | 110 | | | |

| caa | atg | aat | caa | gat | ttg | cag | ggt | tta | acg | agt | ctt | caa | gtt | atg | gat | 384 |
|---|---|---|---|---|---|---|---|---|---|---|---|---|---|---|---|---|
| Gln | Met | Asn | Gln | Asp | Leu | Gln | Gly | Leu | Thr | Ser | Leu | Gln | Val | Met | Asp | |
| | | 115 | | | | | 120 | | | | | 125 | | | | |

| aaa | att | gtt | gca | tat | gct | ggg | cag | att | ggt | ctg | cgt | atc | att | ttg | gat | 432 |
|---|---|---|---|---|---|---|---|---|---|---|---|---|---|---|---|---|
| Lys | Ile | Val | Ala | Tyr | Ala | Gly | Gln | Ile | Gly | Leu | Arg | Ile | Ile | Leu | Asp | |
| | 130 | | | | | 135 | | | | | 140 | | | | | |

| cgg | cat | cgt | cct | gat | tgc | tcc | ggg | cag | tct | gct | ctt | tgg | tac | acc | tcg | 480 |
|---|---|---|---|---|---|---|---|---|---|---|---|---|---|---|---|---|
| Arg | His | Arg | Pro | Asp | Cys | Ser | Gly | Gln | Ser | Ala | Leu | Trp | Tyr | Thr | Ser | |
| 145 | | | | | 150 | | | | | 155 | | | | | 160 | |

| tcc | gtc | agt | gaa | gct | acc | tgg | att | tca | gat | tta | cag | gcg | ttg | gct | cag | 528 |
|---|---|---|---|---|---|---|---|---|---|---|---|---|---|---|---|---|
| Ser | Val | Ser | Glu | Ala | Thr | Trp | Ile | Ser | Asp | Leu | Gln | Ala | Leu | Ala | Gln | |
| | | | | 165 | | | | | 170 | | | | | 175 | | |

| cgg | tat | aaa | ggt | aat | cct | act | gtt | gtt | ggt | ttt | gat | ttg | cat | aac | gaa | 576 |
|---|---|---|---|---|---|---|---|---|---|---|---|---|---|---|---|---|
| Arg | Tyr | Lys | Gly | Asn | Pro | Thr | Val | Val | Gly | Phe | Asp | Leu | His | Asn | Glu | |
| | | | 180 | | | | | 185 | | | | | 190 | | | |

| ccg | cat | gac | ccg | gct | tgc | tgg | ggt | tgt | gga | gat | cct | agc | ata | gat | tgg | 624 |
|---|---|---|---|---|---|---|---|---|---|---|---|---|---|---|---|---|
| Pro | His | Asp | Pro | Ala | Cys | Trp | Gly | Cys | Gly | Asp | Pro | Ser | Ile | Asp | Trp | |
| | | 195 | | | | | 200 | | | | | 205 | | | | |

| cgc | ttg | gcc | gcc | gaa | cgg | gcc | gga | aac | gct | gtc | ctt | tca | gta | aat | ccg | 672 |
|---|---|---|---|---|---|---|---|---|---|---|---|---|---|---|---|---|
| Arg | Leu | Ala | Ala | Glu | Arg | Ala | Gly | Asn | Ala | Val | Leu | Ser | Val | Asn | Pro | |
| | 210 | | | | | 215 | | | | | 220 | | | | | |

| aat | ttg | ttg | att | ttt | gtt | gag | ggt | gtt | caa | tca | tat | aac | ggg | gat | agc | 720 |
|---|---|---|---|---|---|---|---|---|---|---|---|---|---|---|---|---|
| Asn | Leu | Leu | Ile | Phe | Val | Glu | Gly | Val | Gln | Ser | Tyr | Asn | Gly | Asp | Ser | |
| 225 | | | | | 230 | | | | | 235 | | | | | 240 | |

| tat | tgg | tgg | gga | ggg | aat | ctg | caa | gga | gca | ggt | caa | tat | ccc | gtt | gtc | 768 |
|---|---|---|---|---|---|---|---|---|---|---|---|---|---|---|---|---|
| Tyr | Trp | Trp | Gly | Gly | Asn | Leu | Gln | Gly | Ala | Gly | Gln | Tyr | Pro | Val | Val | |
| | | | | 245 | | | | | 250 | | | | | 255 | | |

| ctg | aat | gtc | cct | aac | cgt | ttg | gtt | tat | agc | gcc | cat | gat | tat | gca | acg | 816 |
|---|---|---|---|---|---|---|---|---|---|---|---|---|---|---|---|---|
| Leu | Asn | Val | Pro | Asn | Arg | Leu | Val | Tyr | Ser | Ala | His | Asp | Tyr | Ala | Thr | |
| | | | 260 | | | | | 265 | | | | | 270 | | | |

```
tcg gtt tat ccc caa acc tgg ttt agc gat cca aca ttt cct aat aac      864
Ser Val Tyr Pro Gln Thr Trp Phe Ser Asp Pro Thr Phe Pro Asn Asn
        275                 280                 285 atg ccc ggc att tgg aat aag aac tgg gga tat ctt ttt aat caa aat      912
Met Pro Gly Ile Trp Asn Lys Asn Trp Gly Tyr Leu Phe Asn Gln Asn
290                 295                 300 att gcc ccc gtt tgg ctt ggc gaa ttt ggt act acc ttg cag tct acc      960
Ile Ala Pro Val Trp Leu Gly Glu Phe Gly Thr Thr Leu Gln Ser Thr
305                 310                 315                 320 acc gat cag acc tgg ctt aaa acc tta gtt cag tat tta cgg cct acg     1008
Thr Asp Gln Thr Trp Leu Lys Thr Leu Val Gln Tyr Leu Arg Pro Thr
            325                 330                 335 gcc caa tat ggg gct gat agt ttc cag tgg aca ttt tgg tcc tgg aat     1056
Ala Gln Tyr Gly Ala Asp Ser Phe Gln Trp Thr Phe Trp Ser Trp Asn
                340                 345                 350 ccg gac agt ggc gat acc ggc ggc atc ttg aag gac gac tgg cag aca     1104
Pro Asp Ser Gly Asp Thr Gly Gly Ile Leu Lys Asp Asp Trp Gln Thr
                    355                 360                 365 gtt gat acc gta aaa gat ggt tat ctt gcc ccg atc aag tct tcc atc     1152
Val Asp Thr Val Lys Asp Gly Tyr Leu Ala Pro Ile Lys Ser Ser Ile
370                 375                 380 ttc gac cca gtg ggc gca tct gcc tcc cct tcc tcc caa ccc tcc cct     1200
Phe Asp Pro Val Gly Ala Ser Ala Ser Pro Ser Ser Gln Pro Ser Pro
385                 390                 395                 400 agt gtg agc cca tca ccc agt ccc agt cca agc taa                     1236
Ser Val Ser Pro Ser Pro Ser Pro Ser
                    405                 410

<210> SEQ ID NO 8
<211> LENGTH: 411
<212> TYPE: PRT
<213> ORGANISM: Artificial Sequence
<220> FEATURE:
<223> OTHER INFORMATION: Synthetic Construct

<400> SEQUENCE: 8

Met Lys Arg Lys Leu Gly Arg Arg Gln Leu Leu Thr Gly Phe Val Ala
1               5                   10                  15

Leu Gly Gly Met Ala Ile Thr Ala Gly Lys Ala Gln Ala Ser Ala Gly
            20                  25                  30

Gly Gly Tyr Trp His Thr Ser Gly Arg Glu Ile Leu Asp Ala Asn Asn
        35                  40                  45

Val Pro Val Arg Ile Ala Gly Ile Asn Trp Phe Gly Phe Glu Thr Cys
    50                  55                  60

Asn Tyr Val Val His Gly Leu Trp Ser Arg Asp Tyr Arg Ser Met Leu
65                  70                  75                  80

Asp Gln Ile Lys Ser Leu Gly Tyr Asn Thr Ile Arg Leu Pro Tyr Ser
                85                  90                  95

Asp Asp Ile Leu Lys Pro Gly Thr Met Pro Asn Ser Ile Asn Phe Tyr
            100                 105                 110

Gln Met Asn Gln Asp Leu Gln Gly Leu Thr Ser Leu Gln Val Met Asp
        115                 120                 125

Lys Ile Val Ala Tyr Ala Gly Gln Ile Gly Leu Arg Ile Ile Leu Asp
    130                 135                 140

Arg His Arg Pro Asp Cys Ser Gly Gln Ser Ala Leu Trp Tyr Thr Ser
145                 150                 155                 160

Ser Val Ser Glu Ala Thr Trp Ile Ser Asp Leu Gln Ala Leu Ala Gln
                165                 170                 175
```

```
Arg Tyr Lys Gly Asn Pro Thr Val Val Gly Phe Asp Leu His Asn Glu
            180                 185                 190

Pro His Asp Pro Ala Cys Trp Gly Cys Gly Asp Pro Ser Ile Asp Trp
            195                 200                 205

Arg Leu Ala Ala Glu Arg Ala Gly Asn Ala Val Leu Ser Val Asn Pro
            210                 215                 220

Asn Leu Leu Ile Phe Val Glu Gly Val Gln Ser Tyr Asn Gly Asp Ser
225                 230                 235                 240

Tyr Trp Trp Gly Gly Asn Leu Gln Gly Ala Gly Gln Tyr Pro Val Val
            245                 250                 255

Leu Asn Val Pro Asn Arg Leu Val Tyr Ser Ala His Asp Tyr Ala Thr
            260                 265                 270

Ser Val Tyr Pro Gln Thr Trp Phe Ser Asp Pro Thr Phe Pro Asn Asn
            275                 280                 285

Met Pro Gly Ile Trp Asn Lys Asn Trp Gly Tyr Leu Phe Asn Gln Asn
            290                 295                 300

Ile Ala Pro Val Trp Leu Gly Glu Phe Gly Thr Thr Leu Gln Ser Thr
305                 310                 315                 320

Thr Asp Gln Thr Trp Leu Lys Thr Leu Val Gln Tyr Leu Arg Pro Thr
            325                 330                 335

Ala Gln Tyr Gly Ala Asp Ser Phe Gln Trp Thr Phe Trp Ser Trp Asn
            340                 345                 350

Pro Asp Ser Gly Asp Thr Gly Gly Ile Leu Lys Asp Asp Trp Gln Thr
            355                 360                 365

Val Asp Thr Val Lys Asp Gly Tyr Leu Ala Pro Ile Lys Ser Ser Ile
            370                 375                 380

Phe Asp Pro Val Gly Ala Ser Ala Ser Pro Ser Ser Gln Pro Ser Pro
385                 390                 395                 400

Ser Val Ser Pro Ser Pro Ser Pro Ser
            405                 410

<210> SEQ ID NO 9
<211> LENGTH: 813
<212> TYPE: DNA
<213> ORGANISM: Artificial Sequence
<220> FEATURE:
<223> OTHER INFORMATION: Synthetic fusion sequence
<220> FEATURE:
<221> NAME/KEY: CDS
<222> LOCATION: (1)..(813)

<400> SEQUENCE: 9 atg ata aaa gtc ccg cgg ttc atc tgt atg atc gcg ctt aca tcc agc      48
Met Ile Lys Val Pro Arg Phe Ile Cys Met Ile Ala Leu Thr Ser Ser
1               5                   10                  15 gtt ctg gca agc ggc ctt tct caa agc gtt tca gct cat gct acg acg      96
Val Leu Ala Ser Gly Leu Ser Gln Ser Val Ser Ala His Ala Thr Thr
            20                  25                  30 agc acg tgc agc cca acc gcg gtg gtg agc gtt gca ggc gac gag tac     144
Ser Thr Cys Ser Pro Thr Ala Val Val Ser Val Ala Gly Asp Glu Tyr
        35                  40                  45 cgt gtg caa gct aat gag tgg aat agc tcc gca cag caa tgt ctg acc     192
Arg Val Gln Ala Asn Glu Trp Asn Ser Ser Ala Gln Gln Cys Leu Thr
    50                  55                  60 atc gat acc agc acg ggc gcc tgg agc gtt agc acg gca aac ttt aat     240
Ile Asp Thr Ser Thr Gly Ala Trp Ser Val Ser Thr Ala Asn Phe Asn
65                  70                  75                  80
```

```
ctg gcg acc aat ggt gcg cca gcg acg tat ccg agc att tac aaa ggc      288
Leu Ala Thr Asn Gly Ala Pro Ala Thr Tyr Pro Ser Ile Tyr Lys Gly
            85                  90                  95 tgc cac tgg ggt aac tgc acg acg gca aac gtg ggc atg cct att cag      336
Cys His Trp Gly Asn Cys Thr Thr Ala Asn Val Gly Met Pro Ile Gln
            100                 105                 110 gtt agc aaa att ggt agc gcg gtc acg tcc tgg agc acg acc cag gtt      384
Val Ser Lys Ile Gly Ser Ala Val Thr Ser Trp Ser Thr Thr Gln Val
            115                 120                 125 agc tct ggt gct tat gat gtt gcg tac gat att tgg act aat agc acg      432
Ser Ser Gly Ala Tyr Asp Val Ala Tyr Asp Ile Trp Thr Asn Ser Thr
            130                 135                 140 ccg acc acc agc ggt caa ccg aac ggc acc gag gtc atg att tgg ctg      480
Pro Thr Thr Ser Gly Gln Pro Asn Gly Thr Glu Val Met Ile Trp Leu
145                 150                 155                 160 aac agc cgt ggt ggc gtt caa ccg ttt ggt agc cag acc gcg act ggc      528
Asn Ser Arg Gly Gly Val Gln Pro Phe Gly Ser Gln Thr Ala Thr Gly
            165                 170                 175 gtt acg gtg gct ggc cac acg tgg aac gtt tgg caa ggt cag caa acg      576
Val Thr Val Ala Gly His Thr Trp Asn Val Trp Gln Gly Gln Gln Thr
            180                 185                 190 agc tgg aag att att agc tac gtg ctg acc ccg ggt gcc acc agc att      624
Ser Trp Lys Ile Ile Ser Tyr Val Leu Thr Pro Gly Ala Thr Ser Ile
            195                 200                 205 agc aac ctg gat ctg aaa gcg att ctg gcc gac gcg gct gct cgc ggc      672
Ser Asn Leu Asp Leu Lys Ala Ile Leu Ala Asp Ala Ala Ala Arg Gly
            210                 215                 220 agc ctg aat acc tct gac tat ttg atc gat gtc gaa gct ggt ttc gaa      720
Ser Leu Asn Thr Ser Asp Tyr Leu Ile Asp Val Glu Ala Gly Phe Glu
225                 230                 235                 240 atc tgg caa ggc ggt caa ggt ctg ggt agc aac agc ttt agc gtt tct      768
Ile Trp Gln Gly Gly Gln Gly Leu Gly Ser Asn Ser Phe Ser Val Ser
            245                 250                 255 gtc acg agc ggc act agc agc ccg act ccg acc cct tct taa tga          813
Val Thr Ser Gly Thr Ser Ser Pro Thr Pro Thr Pro Ser
            260                 265

<210> SEQ ID NO 10
<211> LENGTH: 269
<212> TYPE: PRT
<213> ORGANISM: Artificial Sequence
<220> FEATURE:
<223> OTHER INFORMATION: Synthetic Construct

<400> SEQUENCE: 10

Met Ile Lys Val Pro Arg Phe Ile Cys Met Ile Ala Leu Thr Ser Ser
1               5                   10                  15

Val Leu Ala Ser Gly Leu Ser Gln Ser Val Ser Ala His Ala Thr Thr
                20                  25                  30

Ser Thr Cys Ser Pro Thr Ala Val Val Ser Val Ala Gly Asp Glu Tyr
            35                  40                  45

Arg Val Gln Ala Asn Glu Trp Asn Ser Ser Ala Gln Gln Cys Leu Thr
        50                  55                  60

Ile Asp Thr Ser Thr Gly Ala Trp Ser Val Ser Thr Ala Asn Phe Asn
65                  70                  75                  80

Leu Ala Thr Asn Gly Ala Pro Ala Thr Tyr Pro Ser Ile Tyr Lys Gly
                85                  90                  95

Cys His Trp Gly Asn Cys Thr Thr Ala Asn Val Gly Met Pro Ile Gln
            100                 105                 110
```

```
Val Ser Lys Ile Gly Ser Ala Val Thr Ser Trp Ser Thr Gln Val
            115                 120                 125

Ser Ser Gly Ala Tyr Asp Val Ala Tyr Asp Ile Trp Thr Asn Ser Thr
    130                 135                 140

Pro Thr Thr Ser Gly Gln Pro Asn Gly Thr Glu Val Met Ile Trp Leu
145                 150                 155                 160

Asn Ser Arg Gly Gly Val Gln Pro Phe Gly Ser Gln Thr Ala Thr Gly
                165                 170                 175

Val Thr Val Ala Gly His Thr Trp Asn Val Trp Gln Gly Gln Gln Thr
            180                 185                 190

Ser Trp Lys Ile Ile Ser Tyr Val Leu Thr Pro Gly Ala Thr Ser Ile
    195                 200                 205

Ser Asn Leu Asp Leu Lys Ala Ile Leu Ala Asp Ala Ala Arg Gly
210                 215                 220

Ser Leu Asn Thr Ser Asp Tyr Leu Ile Asp Val Glu Ala Gly Phe Glu
225                 230                 235                 240

Ile Trp Gln Gly Gly Gln Gly Leu Gly Ser Asn Ser Phe Ser Val Ser
                245                 250                 255

Val Thr Ser Gly Thr Ser Ser Pro Thr Pro Thr Pro Ser
            260                 265

<210> SEQ ID NO 11
<211> LENGTH: 1146
<212> TYPE: DNA
<213> ORGANISM: Acidothermus cellulolyticus
<220> FEATURE:
<221> NAME/KEY: CDS
<222> LOCATION: (1)..(1146)

<400> SEQUENCE: 11 gcc gga ggg ggt tat tgg cat act tct ggg aga gaa att ttg gac gcg      48
Ala Gly Gly Gly Tyr Trp His Thr Ser Gly Arg Glu Ile Leu Asp Ala
1               5                   10                  15 aat aac gtt ccg gtc cgc att gct ggc atc aat tgg ttt ggt ttt gaa      96
Asn Asn Val Pro Val Arg Ile Ala Gly Ile Asn Trp Phe Gly Phe Glu
                20                  25                  30 acg tgt aac tat gtg gtg cat gga ctg tgg tca cgt gac tat cgg tcg    144
Thr Cys Asn Tyr Val Val His Gly Leu Trp Ser Arg Asp Tyr Arg Ser
            35                  40                  45 atg tta gac cag atc aaa agc tta ggc tat aat acc att cgt ctg cct    192
Met Leu Asp Gln Ile Lys Ser Leu Gly Tyr Asn Thr Ile Arg Leu Pro
        50                  55                  60 tat agc gac gat att ttg aaa ccc ggt acc atg ccc aat agc ata aac    240
Tyr Ser Asp Asp Ile Leu Lys Pro Gly Thr Met Pro Asn Ser Ile Asn
65                  70                  75                  80 ttt tac caa atg aat caa gat ttg cag ggt tta acg agt ctt caa gtt    288
Phe Tyr Gln Met Asn Gln Asp Leu Gln Gly Leu Thr Ser Leu Gln Val
                85                  90                  95 atg gat aaa att gtt gca tat gct ggg cag att ggt ctg cgt atc att    336
Met Asp Lys Ile Val Ala Tyr Ala Gly Gln Ile Gly Leu Arg Ile Ile
            100                 105                 110 ttg gat cgg cat cgt cct gat tgc tcc ggg cag tct gct ctt tgg tac    384
Leu Asp Arg His Arg Pro Asp Cys Ser Gly Gln Ser Ala Leu Trp Tyr
        115                 120                 125 acc tcg tcc gtc agt gaa gct acc tgg att tca gat tta cag gcg ttg    432
Thr Ser Ser Val Ser Glu Ala Thr Trp Ile Ser Asp Leu Gln Ala Leu
    130                 135                 140
```

```
gct cag cgg tat aaa ggt aat cct act gtt gtt ggt ttt gat ttg cat      480
Ala Gln Arg Tyr Lys Gly Asn Pro Thr Val Val Gly Phe Asp Leu His
145             150                 155                 160 aac gaa ccg cat gac ccg gct tgc tgg ggt tgt gga gat cct agc ata      528
Asn Glu Pro His Asp Pro Ala Cys Trp Gly Cys Gly Asp Pro Ser Ile
                165                 170                 175 gat tgg cgc ttg gcc gcc gaa cgg gcc gga aac gct gtc ctt tca gta      576
Asp Trp Arg Leu Ala Ala Glu Arg Ala Gly Asn Ala Val Leu Ser Val
            180                 185                 190 aat ccg aat ttg ttg att ttt gtt gag ggt gtt caa tca tat aac ggg      624
Asn Pro Asn Leu Leu Ile Phe Val Glu Gly Val Gln Ser Tyr Asn Gly
        195                 200                 205 gat agc tat tgg tgg gga ggg aat ctg caa gga gca ggt caa tat ccc      672
Asp Ser Tyr Trp Trp Gly Gly Asn Leu Gln Gly Ala Gly Gln Tyr Pro
    210                 215                 220 gtt gtc ctg aat gtc cct aac cgt ttg gtt tat agc gcc cat gat tat      720
Val Val Leu Asn Val Pro Asn Arg Leu Val Tyr Ser Ala His Asp Tyr
225                 230                 235                 240 gca acg tcg gtt tat ccc caa acc tgg ttt agc gat cca aca ttt cct      768
Ala Thr Ser Val Tyr Pro Gln Thr Trp Phe Ser Asp Pro Thr Phe Pro
                245                 250                 255 aat aac atg ccc ggc att tgg aat aag aac tgg gga tat ctt ttt aat      816
Asn Asn Met Pro Gly Ile Trp Asn Lys Asn Trp Gly Tyr Leu Phe Asn
            260                 265                 270 caa aat att gcc ccc gtt tgg ctt ggc gaa ttt ggt act acc ttg cag      864
Gln Asn Ile Ala Pro Val Trp Leu Gly Glu Phe Gly Thr Thr Leu Gln
        275                 280                 285 tct acc acc gat cag acc tgg ctt aaa acc tta gtt cag tat tta cgg      912
Ser Thr Thr Asp Gln Thr Trp Leu Lys Thr Leu Val Gln Tyr Leu Arg
    290                 295                 300 cct acg gcc caa tat ggg gct gat agt ttc cag tgg aca ttt tgg tcc      960
Pro Thr Ala Gln Tyr Gly Ala Asp Ser Phe Gln Trp Thr Phe Trp Ser
305                 310                 315                 320 tgg aat ccg gac agt ggc gat acc ggc ggc atc ttg aag gac gac tgg     1008
Trp Asn Pro Asp Ser Gly Asp Thr Gly Gly Ile Leu Lys Asp Asp Trp
                325                 330                 335 cag aca gtt gat acc gta aaa gat ggt tat ctt gcc ccg atc aag tct     1056
Gln Thr Val Asp Thr Val Lys Asp Gly Tyr Leu Ala Pro Ile Lys Ser
            340                 345                 350 tcc atc ttc gac cca gtg ggc gca tct gcc tcc cct tcc tcc caa ccc     1104
Ser Ile Phe Asp Pro Val Gly Ala Ser Ala Ser Pro Ser Ser Gln Pro
        355                 360                 365 tcc cct agt gtg agc cca tca ccc agt ccc agt cca agc taa             1146
Ser Pro Ser Val Ser Pro Ser Pro Ser Pro Ser Pro Ser
    370                 375                 380

<210> SEQ ID NO 12
<211> LENGTH: 381
<212> TYPE: PRT
<213> ORGANISM: Acidothermus cellulolyticus

<400> SEQUENCE: 12

Ala Gly Gly Gly Tyr Trp His Thr Ser Gly Arg Glu Ile Leu Asp Ala
1               5                   10                  15

Asn Asn Val Pro Val Arg Ile Ala Gly Ile Asn Trp Phe Gly Phe Glu
                20                  25                  30

Thr Cys Asn Tyr Val Val His Gly Leu Trp Ser Arg Asp Tyr Arg Ser
            35                  40                  45

Met Leu Asp Gln Ile Lys Ser Leu Gly Tyr Asn Thr Ile Arg Leu Pro
        50                  55                  60
```

-continued

```
Tyr Ser Asp Asp Ile Leu Lys Pro Gly Thr Met Pro Asn Ser Ile Asn
 65                  70                  75                  80

Phe Tyr Gln Met Asn Gln Asp Leu Gln Gly Leu Thr Ser Leu Gln Val
                 85                  90                  95

Met Asp Lys Ile Val Ala Tyr Ala Gly Gln Ile Gly Leu Arg Ile Ile
            100                 105                 110

Leu Asp Arg His Arg Pro Asp Cys Ser Gly Gln Ser Ala Leu Trp Tyr
        115                 120                 125

Thr Ser Ser Val Ser Glu Ala Thr Trp Ile Ser Asp Leu Gln Ala Leu
130                 135                 140

Ala Gln Arg Tyr Lys Gly Asn Pro Thr Val Val Gly Phe Asp Leu His
145                 150                 155                 160

Asn Glu Pro His Asp Pro Ala Cys Trp Gly Cys Gly Asp Pro Ser Ile
                165                 170                 175

Asp Trp Arg Leu Ala Ala Glu Arg Ala Gly Asn Ala Val Leu Ser Val
            180                 185                 190

Asn Pro Asn Leu Leu Ile Phe Val Glu Gly Val Gln Ser Tyr Asn Gly
        195                 200                 205

Asp Ser Tyr Trp Trp Gly Gly Asn Leu Gln Gly Ala Gly Gln Tyr Pro
210                 215                 220

Val Val Leu Asn Val Pro Asn Arg Leu Val Tyr Ser Ala His Asp Tyr
225                 230                 235                 240

Ala Thr Ser Val Tyr Pro Gln Thr Trp Phe Ser Asp Pro Thr Phe Pro
                245                 250                 255

Asn Asn Met Pro Gly Ile Trp Asn Lys Asn Trp Gly Tyr Leu Phe Asn
            260                 265                 270

Gln Asn Ile Ala Pro Val Trp Leu Gly Glu Phe Gly Thr Thr Leu Gln
        275                 280                 285

Ser Thr Thr Asp Gln Thr Trp Leu Lys Thr Leu Val Gln Tyr Leu Arg
290                 295                 300

Pro Thr Ala Gln Tyr Gly Ala Asp Ser Phe Gln Trp Thr Phe Trp Ser
305                 310                 315                 320

Trp Asn Pro Asp Ser Gly Asp Thr Gly Gly Ile Leu Lys Asp Asp Trp
                325                 330                 335

Gln Thr Val Asp Thr Val Lys Asp Gly Tyr Leu Ala Pro Ile Lys Ser
            340                 345                 350

Ser Ile Phe Asp Pro Val Gly Ala Ser Ala Ser Pro Ser Ser Gln Pro
        355                 360                 365

Ser Pro Ser Val Ser Pro Ser Pro Ser Pro Ser
370                 375                 380

<210> SEQ ID NO 13
<211> LENGTH: 729
<212> TYPE: DNA
<213> ORGANISM: Acidothermus cellulolyticus
<220> FEATURE:
<221> NAME/KEY: CDS
<222> LOCATION: (1)..(729)

<400> SEQUENCE: 13 atg gct acg acg agc acg tgc agc cca acc gcg gtg gtg agc gtt gca    48
Met Ala Thr Thr Ser Thr Cys Ser Pro Thr Ala Val Val Ser Val Ala
  1               5                  10                  15 ggc gac gag tac cgt gtg caa gct aat gag tgg aat agc tcc gca cag    96
Gly Asp Glu Tyr Arg Val Gln Ala Asn Glu Trp Asn Ser Ser Ala Gln
             20                  25                  30
```

```
caa tgt ctg acc atc gat acc agc acg ggc gcc tgg agc gtt agc acg    144
Gln Cys Leu Thr Ile Asp Thr Ser Thr Gly Ala Trp Ser Val Ser Thr
         35                  40                  45 gca aac ttt aat ctg gcg acc aat ggt gcg cca gcg acg tat ccg agc    192
Ala Asn Phe Asn Leu Ala Thr Asn Gly Ala Pro Ala Thr Tyr Pro Ser
 50                  55                  60 att tac aaa ggc tgc cac tgg ggt aac tgc acg acg gca aac gtg ggc    240
Ile Tyr Lys Gly Cys His Trp Gly Asn Cys Thr Thr Ala Asn Val Gly
 65                  70                  75                  80 atg cct att cag gtt agc aaa att ggt agc gcg gtc acg tcc tgg agc    288
Met Pro Ile Gln Val Ser Lys Ile Gly Ser Ala Val Thr Ser Trp Ser
                 85                  90                  95 acg acc cag gtt agc tct ggt gct tat gat gtt gcg tac gat att tgg    336
Thr Thr Gln Val Ser Ser Gly Ala Tyr Asp Val Ala Tyr Asp Ile Trp
            100                 105                 110 act aat agc acg ccg acc acc agc ggt caa ccg aac ggc acc gag gtc    384
Thr Asn Ser Thr Pro Thr Thr Ser Gly Gln Pro Asn Gly Thr Glu Val
        115                 120                 125 atg att tgg ctg aac agc cgt ggt ggc gtt caa ccg ttt ggt agc cag    432
Met Ile Trp Leu Asn Ser Arg Gly Gly Val Gln Pro Phe Gly Ser Gln
    130                 135                 140 acc gcg act ggc gtt acg gtg gct ggc cac acg tgg aac gtt tgg caa    480
Thr Ala Thr Gly Val Thr Val Ala Gly His Thr Trp Asn Val Trp Gln
145                 150                 155                 160 ggt cag caa acg agc tgg aag att att agc tac gtg ctg acc ccg ggt    528
Gly Gln Gln Thr Ser Trp Lys Ile Ile Ser Tyr Val Leu Thr Pro Gly
                165                 170                 175 gcc acc agc att agc aac ctg gat ctg aaa gcg att ctg gcc gac gcg    576
Ala Thr Ser Ile Ser Asn Leu Asp Leu Lys Ala Ile Leu Ala Asp Ala
            180                 185                 190 gct gct cgc ggc agc ctg aat acc tct gac tat ttg atc gat gtc gaa    624
Ala Ala Arg Gly Ser Leu Asn Thr Ser Asp Tyr Leu Ile Asp Val Glu
        195                 200                 205 gct ggt ttc gaa atc tgg caa ggc ggt caa ggt ctg ggt agc aac agc    672
Ala Gly Phe Glu Ile Trp Gln Gly Gly Gln Gly Leu Gly Ser Asn Ser
    210                 215                 220 ttt agc gtt tct gtc acg agc ggc act agc agc ccg act ccg acc cct    720
Phe Ser Val Ser Val Thr Ser Gly Thr Ser Ser Pro Thr Pro Thr Pro
225                 230                 235                 240 tct taa tga                                                        729
Ser

<210> SEQ ID NO 14
<211> LENGTH: 241
<212> TYPE: PRT
<213> ORGANISM: Acidothermus cellulolyticus

<400> SEQUENCE: 14

Met Ala Thr Thr Ser Thr Cys Ser Pro Thr Ala Val Val Ser Val Ala
 1               5                  10                  15

Gly Asp Glu Tyr Arg Val Gln Ala Asn Glu Trp Asn Ser Ser Ala Gln
                20                  25                  30

Gln Cys Leu Thr Ile Asp Thr Ser Thr Gly Ala Trp Ser Val Ser Thr
         35                  40                  45

Ala Asn Phe Asn Leu Ala Thr Asn Gly Ala Pro Ala Thr Tyr Pro Ser
 50                  55                  60

Ile Tyr Lys Gly Cys His Trp Gly Asn Cys Thr Thr Ala Asn Val Gly
 65                  70                  75                  80
```

```
Met Pro Ile Gln Val Ser Lys Ile Gly Ser Ala Val Thr Ser Trp Ser
             85                  90                  95

Thr Thr Gln Val Ser Ser Gly Ala Tyr Asp Val Ala Tyr Asp Ile Trp
            100                 105                 110

Thr Asn Ser Thr Pro Thr Thr Ser Gly Gln Pro Asn Gly Thr Glu Val
        115                 120                 125

Met Ile Trp Leu Asn Ser Arg Gly Gly Val Gln Pro Phe Gly Ser Gln
    130                 135                 140

Thr Ala Thr Gly Val Thr Val Ala Gly His Thr Trp Asn Val Trp Gln
145                 150                 155                 160

Gly Gln Gln Thr Ser Trp Lys Ile Ile Ser Tyr Val Leu Thr Pro Gly
                165                 170                 175

Ala Thr Ser Ile Ser Asn Leu Asp Leu Lys Ala Ile Leu Ala Asp Ala
            180                 185                 190

Ala Ala Arg Gly Ser Leu Asn Thr Ser Asp Tyr Leu Ile Asp Val Glu
        195                 200                 205

Ala Gly Phe Glu Ile Trp Gln Gly Gly Gln Gly Leu Gly Ser Asn Ser
    210                 215                 220

Phe Ser Val Ser Val Thr Ser Gly Thr Ser Ser Pro Thr Pro Thr Pro
225                 230                 235                 240

Ser
```

```
<210> SEQ ID NO 15
<211> LENGTH: 73
<212> TYPE: DNA
<213> ORGANISM: Escherichia coli

<400> SEQUENCE: 15
ttgacaatta atcatcggct cgtataatgt gtggaattgt gagcggataa caatttcaca     60
caggagatat cat                                                        73

<210> SEQ ID NO 16
<211> LENGTH: 205
<212> TYPE: DNA
<213> ORGANISM: Escherichia coli

<400> SEQUENCE: 16
aggcatcaaa taaaacgaaa ggctcagtcg aaagactggg cctttcgttt tatctgttgt     60
ttgtcggtga acgctctcct gagtaggaca atccgccgg gagcggattt gaacgttgcg    120
aagcaacggc ccggagggtg gcgggcagga cgcccgccat aaactgccag gcatcaaatt    180
aagcagaagg ccatcctgac ggatg                                          205

<210> SEQ ID NO 17
<211> LENGTH: 1511
<212> TYPE: DNA
<213> ORGANISM: Artificial Sequence
<220> FEATURE:
<223> OTHER INFORMATION: Synthetic fusion sequence
<220> FEATURE:
<221> NAME/KEY: CDS
<222> LOCATION: (74)..(1306)

<400> SEQUENCE: 17
ttgacaatta atcatcggct cgtataatgt gtggaattgt gagcggataa caatttcaca     60
caggagatat cat atg ata aaa gtc ccg cgg ttc atc tgt atg atc gcg    109
               Met Ile Lys Val Pro Arg Phe Ile Cys Met Ile Ala
                 1               5                  10
```

| | |
|---|---|
| ctt aca tcc agc gtt ctg gca agc ggc ctt tct caa agc gtt tca gct<br>Leu Thr Ser Ser Val Leu Ala Ser Gly Leu Ser Gln Ser Val Ser Ala<br>        15                  20                  25 | 157 |
| cat gcc gga ggg ggt tat tgg cat act tct ggg aga gaa att ttg gac<br>His Ala Gly Gly Gly Tyr Trp His Thr Ser Gly Arg Glu Ile Leu Asp<br> 30                       35                 40 | 205 |
| gcg aat aac gtt ccg gtc cgc att gct ggc atc aat tgg ttt ggt ttt<br>Ala Asn Asn Val Pro Val Arg Ile Ala Gly Ile Asn Trp Phe Gly Phe<br>45                   50                 55                 60 | 253 |
| gaa acg tgt aac tat gtg gtg cat gga ctg tgg tca cgt gac tat cgg<br>Glu Thr Cys Asn Tyr Val Val His Gly Leu Trp Ser Arg Asp Tyr Arg<br>               65                 70                 75 | 301 |
| tcg atg tta gac cag atc aaa agc tta ggc tat aat acc att cgt ctg<br>Ser Met Leu Asp Gln Ile Lys Ser Leu Gly Tyr Asn Thr Ile Arg Leu<br>                  80                 85                 90 | 349 |
| cct tat agc gac gat att ttg aaa ccc ggt acc atg ccc aat agc ata<br>Pro Tyr Ser Asp Asp Ile Leu Lys Pro Gly Thr Met Pro Asn Ser Ile<br>            95                  100                105 | 397 |
| aac ttt tac caa atg aat caa gat ttg cag ggt tta acg agt ctt caa<br>Asn Phe Tyr Gln Met Asn Gln Asp Leu Gln Gly Leu Thr Ser Leu Gln<br>        110                  115                120 | 445 |
| gtt atg gat aaa att gtt gca tat gct ggg cag att ggt ctg cgt atc<br>Val Met Asp Lys Ile Val Ala Tyr Ala Gly Gln Ile Gly Leu Arg Ile<br>125                  130                135                140 | 493 |
| att ttg gat cgg cat cgt cct gat tgc tcc ggg cag tct gct ctt tgg<br>Ile Leu Asp Arg His Arg Pro Asp Cys Ser Gly Gln Ser Ala Leu Trp<br>                  145                150                155 | 541 |
| tac acc tcg tcc gtc agt gaa gct acc tgg att tca gat tta cag gcg<br>Tyr Thr Ser Ser Val Ser Glu Ala Thr Trp Ile Ser Asp Leu Gln Ala<br>              160                165                170 | 589 |
| ttg gct cag cgg tat aaa ggt aat cct act gtt gtt ggt ttt gat ttg<br>Leu Ala Gln Arg Tyr Lys Gly Asn Pro Thr Val Val Gly Phe Asp Leu<br>        175                  180                185 | 637 |
| cat aac gaa ccg cat gac ccg gct tgc tgg ggt tgt gga gat cct agc<br>His Asn Glu Pro His Asp Pro Ala Cys Trp Gly Cys Gly Asp Pro Ser<br>              190                195                200 | 685 |
| ata gat tgg cgc ttg gcc gcc gaa cgg gcc gga aac gct gtc ctt tca<br>Ile Asp Trp Arg Leu Ala Ala Glu Arg Ala Gly Asn Ala Val Leu Ser<br>205                  210                215                220 | 733 |
| gta aat ccg aat ttg ttg att ttt gtt gag ggt gtt caa tca tat aac<br>Val Asn Pro Asn Leu Leu Ile Phe Val Glu Gly Val Gln Ser Tyr Asn<br>              225                230                235 | 781 |
| ggg gat agc tat tgg tgg gga ggg aat ctg caa gga gca ggt caa tat<br>Gly Asp Ser Tyr Trp Trp Gly Gly Asn Leu Gln Gly Ala Gly Gln Tyr<br>        240                  245                250 | 829 |
| ccc gtt gtc ctg aat gtc cct aac cgt ttg gtt tat agc gcc cat gat<br>Pro Val Val Leu Asn Val Pro Asn Arg Leu Val Tyr Ser Ala His Asp<br>              255                260                265 | 877 |
| tat gca acg tcg gtt tat ccc caa acc tgg ttt agc gat cca aca ttt<br>Tyr Ala Thr Ser Val Tyr Pro Gln Thr Trp Phe Ser Asp Pro Thr Phe<br>        270                  275                280 | 925 |
| cct aat aac atg ccc ggc att tgg aat aag aac tgg gga tat ctt ttt<br>Pro Asn Asn Met Pro Gly Ile Trp Asn Lys Asn Trp Gly Tyr Leu Phe<br>285                  290                295                300 | 973 |
| aat caa aat att gcc ccc gtt tgg ctt ggc gaa ttt ggt act acc ttg<br>Asn Gln Asn Ile Ala Pro Val Trp Leu Gly Glu Phe Gly Thr Thr Leu<br>                  305                310                315 | 1021 |
| cag tct acc acc gat cag acc tgg ctt aaa acc tta gtt cag tat tta<br>Gln Ser Thr Thr Asp Gln Thr Trp Leu Lys Thr Leu Val Gln Tyr Leu<br>        320                  325                330 | 1069 |

```
cgg cct acg gcc caa tat ggg gct gat agt ttc cag tgg aca ttt tgg    1117
Arg Pro Thr Ala Gln Tyr Gly Ala Asp Ser Phe Gln Trp Thr Phe Trp
        335                 340                 345 tcc tgg aat ccg gac agt ggc gat acc ggc ggc atc ttg aag gac gac    1165
Ser Trp Asn Pro Asp Ser Gly Asp Thr Gly Gly Ile Leu Lys Asp Asp
350                 355                 360 tgg cag aca gtt gat acc gta aaa gat ggt tat ctt gcc ccg atc aag    1213
Trp Gln Thr Val Asp Thr Val Lys Asp Gly Tyr Leu Ala Pro Ile Lys
365                 370                 375                 380 tct tcc atc ttc gac cca gtg ggc gca tct gcc tcc cct tcc tcc caa    1261
Ser Ser Ile Phe Asp Pro Val Gly Ala Ser Ala Ser Pro Ser Ser Gln
            385                 390                 395 ccc tcc cct agt gtg agc cca tca ccc agt ccc agt cca agc taa        1306
Pro Ser Pro Ser Val Ser Pro Ser Pro Ser Pro Ser Pro Ser
                400                 405                 410 aggcatcaaa taaacgaaa ggctcagtcg aaagactggg cctttcgttt tatctgttgt    1366
ttgtcggtga acgctctcct gagtaggaca atccgccgg gagcggattt gaacgttgcg    1426
aagcaacggc ccggagggtg gcgggcagga cgcccgccat aaactgccag gcatcaaatt   1486
aagcagaagg ccatcctgac ggatg                                        1511

<210> SEQ ID NO 18
<211> LENGTH: 410
<212> TYPE: PRT
<213> ORGANISM: Artificial Sequence
<220> FEATURE:
<223> OTHER INFORMATION: Synthetic Construct

<400> SEQUENCE: 18

Met Ile Lys Val Pro Arg Phe Ile Cys Met Ile Ala Leu Thr Ser Ser
1               5                   10                  15

Val Leu Ala Ser Gly Leu Ser Gln Ser Val Ser Ala His Ala Gly Gly
            20                  25                  30

Gly Tyr Trp His Thr Ser Gly Arg Glu Ile Leu Asp Ala Asn Asn Val
        35                  40                  45

Pro Val Arg Ile Ala Gly Ile Asn Trp Phe Gly Phe Glu Thr Cys Asn
    50                  55                  60

Tyr Val Val His Gly Leu Trp Ser Arg Asp Tyr Arg Ser Met Leu Asp
65                  70                  75                  80

Gln Ile Lys Ser Leu Gly Tyr Asn Thr Ile Arg Leu Pro Tyr Ser Asp
                85                  90                  95

Asp Ile Leu Lys Pro Gly Thr Met Pro Asn Ser Ile Asn Phe Tyr Gln
            100                 105                 110

Met Asn Gln Asp Leu Gln Gly Leu Thr Ser Leu Gln Val Met Asp Lys
        115                 120                 125

Ile Val Ala Tyr Ala Gly Gln Ile Gly Leu Arg Ile Ile Leu Asp Arg
    130                 135                 140

His Arg Pro Asp Cys Ser Gly Gln Ser Ala Leu Trp Tyr Thr Ser Ser
145                 150                 155                 160

Val Ser Glu Ala Thr Trp Ile Ser Asp Leu Gln Ala Leu Ala Gln Arg
                165                 170                 175

Tyr Lys Gly Asn Pro Thr Val Val Gly Phe Asp Leu His Asn Glu Pro
            180                 185                 190

His Asp Pro Ala Cys Trp Gly Cys Gly Asp Pro Ser Ile Asp Trp Arg
        195                 200                 205

Leu Ala Ala Glu Arg Ala Gly Asn Ala Val Leu Ser Val Asn Pro Asn
    210                 215                 220
```

```
Leu Leu Ile Phe Val Glu Gly Val Gln Ser Tyr Asn Gly Asp Ser Tyr
225                 230                 235                 240

Trp Trp Gly Gly Asn Leu Gln Gly Ala Gly Gln Tyr Pro Val Val Leu
                245                 250                 255

Asn Val Pro Asn Arg Leu Val Tyr Ser Ala His Asp Tyr Ala Thr Ser
            260                 265                 270

Val Tyr Pro Gln Thr Trp Phe Ser Asp Pro Thr Phe Pro Asn Asn Met
        275                 280                 285

Pro Gly Ile Trp Asn Lys Asn Trp Gly Tyr Leu Phe Asn Gln Asn Ile
    290                 295                 300

Ala Pro Val Trp Leu Gly Glu Phe Gly Thr Thr Leu Gln Ser Thr Thr
305                 310                 315                 320

Asp Gln Thr Trp Leu Lys Thr Leu Val Gln Tyr Leu Arg Pro Thr Ala
                325                 330                 335

Gln Tyr Gly Ala Asp Ser Phe Gln Trp Thr Phe Trp Ser Trp Asn Pro
            340                 345                 350

Asp Ser Gly Asp Thr Gly Gly Ile Leu Lys Asp Trp Gln Thr Val
        355                 360                 365

Asp Thr Val Lys Asp Gly Tyr Leu Ala Pro Ile Lys Ser Ser Ile Phe
370                 375                 380

Asp Pro Val Gly Ala Ser Ala Ser Pro Ser Ser Gln Pro Ser Pro Ser
385                 390                 395                 400

Val Ser Pro Ser Pro Ser Pro Ser
                405                 410

<210> SEQ ID NO 19
<211> LENGTH: 1514
<212> TYPE: DNA
<213> ORGANISM: Artificial Sequence
<220> FEATURE:
<223> OTHER INFORMATION: Synthetic fusion sequence
<220> FEATURE:
<221> NAME/KEY: CDS
<222> LOCATION: (74)..(1309)

<400> SEQUENCE: 19
ttgacaatta atcatcggct cgtataatgt gtggaattgt gagcggataa caatttcaca       60 cag gag ata t cat atg aaa aga aag ctt ggt cgt cgc cag tta tta act      109
              Met Lys Arg Lys Leu Gly Arg Arg Gln Leu Leu Thr
              1               5                   10 ggc ttt gtt gcc ctt ggc ggt atg gcg att aca gct ggt aag gcg cag       157
Gly Phe Val Ala Leu Gly Gly Met Ala Ile Thr Ala Gly Lys Ala Gln
        15                  20                  25 gct tct gcc gga ggg ggt tat tgg cat act tct ggg aga gaa att ttg       205
Ala Ser Ala Gly Gly Gly Tyr Trp His Thr Ser Gly Arg Glu Ile Leu
30                  35                  40 gac gcg aat aac gtt ccg gtc cgc att gct ggc atc aat tgg ttt ggt       253
Asp Ala Asn Asn Val Pro Val Arg Ile Ala Gly Ile Asn Trp Phe Gly
45                  50                  55                  60 ttt gaa acg tgt aac tat gtg gtg cat gga ctg tgg tca cgt gac tat       301
Phe Glu Thr Cys Asn Tyr Val Val His Gly Leu Trp Ser Arg Asp Tyr
                65                  70                  75 cgg tcg atg tta gac cag atc aaa agc tta ggc tat aat acc att cgt       349
Arg Ser Met Leu Asp Gln Ile Lys Ser Leu Gly Tyr Asn Thr Ile Arg
            80                  85                  90 ctg cct tat agc gac gat att ttg aaa ccc ggt acc atg ccc aat agc       397
Leu Pro Tyr Ser Asp Asp Ile Leu Lys Pro Gly Thr Met Pro Asn Ser
        95                  100                 105
```

-continued

| | |
|---|---|
| ata aac ttt tac caa atg aat caa gat ttg cag ggt tta acg agt ctt<br>Ile Asn Phe Tyr Gln Met Asn Gln Asp Leu Gln Gly Leu Thr Ser Leu<br>110              115              120 | 445 |
| caa gtt atg gat aaa att gtt gca tat gct ggg cag att ggt ctg cgt<br>Gln Val Met Asp Lys Ile Val Ala Tyr Ala Gly Gln Ile Gly Leu Arg<br>125              130              135              140 | 493 |
| atc att ttg gat cgg cat cgt cct gat tgc tcc ggg cag tct gct ctt<br>Ile Ile Leu Asp Arg His Arg Pro Asp Cys Ser Gly Gln Ser Ala Leu<br>                 145              150              155 | 541 |
| tgg tac acc tcg tcc gtc agt gaa gct acc tgg att tca gat tta cag<br>Trp Tyr Thr Ser Ser Val Ser Glu Ala Thr Trp Ile Ser Asp Leu Gln<br>     160              165              170 | 589 |
| gcg ttg gct cag cgg tat aaa ggt aat cct act gtt gtt ggt ttt gat<br>Ala Leu Ala Gln Arg Tyr Lys Gly Asn Pro Thr Val Val Gly Phe Asp<br>175              180              185 | 637 |
| ttg cat aac gaa ccg cat gac ccg gct tgc tgg ggt tgt gga gat cct<br>Leu His Asn Glu Pro His Asp Pro Ala Cys Trp Gly Cys Gly Asp Pro<br>    190              195              200 | 685 |
| agc ata gat tgg cgc ttg gcc gcc gaa cgg gcc gga aac gct gtc ctt<br>Ser Ile Asp Trp Arg Leu Ala Ala Glu Arg Ala Gly Asn Ala Val Leu<br>205              210              215              220 | 733 |
| tca gta aat ccg aat ttg ttg att ttt gtt gag ggt gtt caa tca tat<br>Ser Val Asn Pro Asn Leu Leu Ile Phe Val Glu Gly Val Gln Ser Tyr<br>                 225              230              235 | 781 |
| aac ggg gat agc tat tgg tgg gga ggg aat ctg caa gga gca ggt caa<br>Asn Gly Asp Ser Tyr Trp Trp Gly Gly Asn Leu Gln Gly Ala Gly Gln<br>     240              245              250 | 829 |
| tat ccc gtt gtc ctg aat gtc cct aac cgt ttg gtt tat agc gcc cat<br>Tyr Pro Val Val Leu Asn Val Pro Asn Arg Leu Val Tyr Ser Ala His<br>255              260              265 | 877 |
| gat tat gca acg tcg gtt tat ccc caa acc tgg ttt agc gat cca aca<br>Asp Tyr Ala Thr Ser Val Tyr Pro Gln Thr Trp Phe Ser Asp Pro Thr<br>    270              275              280 | 925 |
| ttt cct aat aac atg ccc ggc att tgg aat aag aac tgg gga tat ctt<br>Phe Pro Asn Asn Met Pro Gly Ile Trp Asn Lys Asn Trp Gly Tyr Leu<br>285              290              295              300 | 973 |
| ttt aat caa aat att gcc ccc gtt tgg ctt ggc gaa ttt ggt act acc<br>Phe Asn Gln Asn Ile Ala Pro Val Trp Leu Gly Glu Phe Gly Thr Thr<br>                 305              310              315 | 1021 |
| ttg cag tct acc acc gat cag acc tgg ctt aaa acc tta gtt cag tat<br>Leu Gln Ser Thr Thr Asp Gln Thr Trp Leu Lys Thr Leu Val Gln Tyr<br>     320              325              330 | 1069 |
| tta cgg cct acg gcc caa tat ggg gct gat agt ttc cag tgg aca ttt<br>Leu Arg Pro Thr Ala Gln Tyr Gly Ala Asp Ser Phe Gln Trp Thr Phe<br>335              340              345 | 1117 |
| tgg tcc tgg aat ccg gac agt ggc gat acc ggc ggc atc ttg aag gac<br>Trp Ser Trp Asn Pro Asp Ser Gly Asp Thr Gly Gly Ile Leu Lys Asp<br>    350              355              360 | 1165 |
| gac tgg cag aca gtt gat acc gta aaa gat ggt tat ctt gcc ccg atc<br>Asp Trp Gln Thr Val Asp Thr Val Lys Asp Gly Tyr Leu Ala Pro Ile<br>365              370              375              380 | 1213 |
| aag tct tcc atc ttc gac cca gtg ggc gca tct gcc tcc cct tcc tcc<br>Lys Ser Ser Ile Phe Asp Pro Val Gly Ala Ser Ala Ser Pro Ser Ser<br>                 385              390              395 | 1261 |
| caa ccc tcc cct agt gtg agc cca tca ccc agt ccc agt cca agc taa<br>Gln Pro Ser Pro Ser Val Ser Pro Ser Pro Ser Pro Ser Pro Ser<br>     400              405              410 | 1309 |
| aggcatcaaa taaaacgaaa ggctcagtcg aaagactggg cctttcgttt tatctgttgt | 1369 |
| ttgtcggtga acgctctcct gagtaggaca aatccgccgg gagcggattt gaacgttgcg | 1429 | aagcaacggc ccggagggtg gcgggcagga cgcccgccat aaactgccag gcatcaaatt    1489 aagcagaagg ccatcctgac ggatg                                         1514

<210> SEQ ID NO 20
<211> LENGTH: 411
<212> TYPE: PRT
<213> ORGANISM: Artificial Sequence
<220> FEATURE:
<223> OTHER INFORMATION: Synthetic Construct

<400> SEQUENCE: 20

Met Lys Arg Lys Leu Gly Arg Arg Gln Leu Leu Thr Gly Phe Val Ala
1               5                   10                  15

Leu Gly Gly Met Ala Ile Thr Ala Gly Lys Ala Gln Ala Ser Ala Gly
            20                  25                  30

Gly Gly Tyr Trp His Thr Ser Gly Arg Glu Ile Leu Asp Ala Asn Asn
        35                  40                  45

Val Pro Val Arg Ile Ala Gly Ile Asn Trp Phe Gly Phe Glu Thr Cys
    50                  55                  60

Asn Tyr Val Val His Gly Leu Trp Ser Arg Asp Tyr Arg Ser Met Leu
65                  70                  75                  80

Asp Gln Ile Lys Ser Leu Gly Tyr Asn Thr Ile Arg Leu Pro Tyr Ser
                85                  90                  95

Asp Asp Ile Leu Lys Pro Gly Thr Met Pro Asn Ser Ile Asn Phe Tyr
            100                 105                 110

Gln Met Asn Gln Asp Leu Gln Gly Leu Thr Ser Leu Gln Val Met Asp
        115                 120                 125

Lys Ile Val Ala Tyr Ala Gly Gln Ile Gly Leu Arg Ile Ile Leu Asp
    130                 135                 140

Arg His Arg Pro Asp Cys Ser Gly Gln Ser Ala Leu Trp Tyr Thr Ser
145                 150                 155                 160

Ser Val Ser Glu Ala Thr Trp Ile Ser Asp Leu Gln Ala Leu Ala Gln
                165                 170                 175

Arg Tyr Lys Gly Asn Pro Thr Val Val Gly Phe Asp Leu His Asn Glu
            180                 185                 190

Pro His Asp Pro Ala Cys Trp Gly Cys Gly Asp Pro Ser Ile Asp Trp
        195                 200                 205

Arg Leu Ala Ala Glu Arg Ala Gly Asn Ala Val Leu Ser Val Asn Pro
    210                 215                 220

Asn Leu Leu Ile Phe Val Glu Gly Val Gln Ser Tyr Asn Gly Asp Ser
225                 230                 235                 240

Tyr Trp Trp Gly Gly Asn Leu Gln Gly Ala Gly Gln Tyr Pro Val Val
                245                 250                 255

Leu Asn Val Pro Asn Arg Leu Val Tyr Ser Ala His Asp Tyr Ala Thr
            260                 265                 270

Ser Val Tyr Pro Gln Thr Trp Phe Ser Asp Pro Thr Phe Pro Asn Asn
        275                 280                 285

Met Pro Gly Ile Trp Asn Lys Asn Trp Gly Tyr Leu Phe Asn Gln Asn
    290                 295                 300

Ile Ala Pro Val Trp Leu Gly Glu Phe Gly Thr Thr Leu Gln Ser Thr
305                 310                 315                 320

Thr Asp Gln Thr Trp Leu Lys Thr Leu Val Gln Tyr Leu Arg Pro Thr
                325                 330                 335

Ala Gln Tyr Gly Ala Asp Ser Phe Gln Trp Thr Phe Trp Ser Trp Asn
            340                 345                 350

```
Pro Asp Ser Gly Asp Thr Gly Ile Leu Lys Asp Trp Gln Thr
            355                 360                 365
Val Asp Thr Val Lys Asp Gly Tyr Leu Ala Pro Ile Lys Ser Ser Ile
    370                 375                 380
Phe Asp Pro Val Gly Ala Ser Ala Ser Pro Ser Ser Gln Pro Ser Pro
385                 390                 395                 400
Ser Val Ser Pro Ser Pro Ser Pro Ser
                405                 410

<210> SEQ ID NO 21
<211> LENGTH: 1091
<212> TYPE: DNA
<213> ORGANISM: Artificial Sequence
<220> FEATURE:
<223> OTHER INFORMATION: Synthetic fusion sequence
<220> FEATURE:
<221> NAME/KEY: CDS
<222> LOCATION: (74)..(886)

<400> SEQUENCE: 21
ttgacaatta atcatcggct cgtataatgt gtggaattgt gagcggataa caatttcaca       60
caggagatat cat atg ata aaa gtc ccg cgg ttc atc tgt atg atc gcg         109
            Met Ile Lys Val Pro Arg Phe Ile Cys Met Ile Ala
             1               5                  10 ctt aca tcc agc gtt ctg gca agc ggc ctt tct caa agc gtt tca gct       157
Leu Thr Ser Ser Val Leu Ala Ser Gly Leu Ser Gln Ser Val Ser Ala
        15                  20                  25 cat gct acg acg agc acg tgc agc cca acc gcg gtg gtg agc gtt gca       205
His Ala Thr Thr Ser Thr Cys Ser Pro Thr Ala Val Val Ser Val Ala
         30                  35                  40 ggc gac gag tac cgt gtg caa gct aat gag tgg aat agc tcc gca cag       253
Gly Asp Glu Tyr Arg Val Gln Ala Asn Glu Trp Asn Ser Ser Ala Gln
 45                  50                  55                  60 caa tgt ctg acc atc gat acc agc acg ggc gcc tgg agc gtt agc acg       301
Gln Cys Leu Thr Ile Asp Thr Ser Thr Gly Ala Trp Ser Val Ser Thr
                 65                  70                  75 gca aac ttt aat ctg gcg acc aat ggt gcg cca gcg acg tat ccg agc       349
Ala Asn Phe Asn Leu Ala Thr Asn Gly Ala Pro Ala Thr Tyr Pro Ser
             80                  85                  90 att tac aaa ggc tgc cac tgg ggt aac tgc acg acg gca aac gtg ggc       397
Ile Tyr Lys Gly Cys His Trp Gly Asn Cys Thr Thr Ala Asn Val Gly
         95                 100                 105 atg cct att cag gtt agc aaa att ggt agc gcg gtc acg tcc tgg agc       445
Met Pro Ile Gln Val Ser Lys Ile Gly Ser Ala Val Thr Ser Trp Ser
    110                 115                 120 acg acc cag gtt agc tct ggt gct tat gat gtt gcg tac gat att tgg       493
Thr Thr Gln Val Ser Ser Gly Ala Tyr Asp Val Ala Tyr Asp Ile Trp
125                 130                 135                 140 act aat agc acg ccg acc acc agc ggt caa ccg aac ggc acc gag gtc       541
Thr Asn Ser Thr Pro Thr Thr Ser Gly Gln Pro Asn Gly Thr Glu Val
                145                 150                 155 atg att tgg ctg aac agc cgt ggt ggc gtt caa ccg ttt ggt agc cag       589
Met Ile Trp Leu Asn Ser Arg Gly Gly Val Gln Pro Phe Gly Ser Gln
            160                 165                 170 acc gcg act ggc gtt acg gtg gct ggc cac acg tgg aac gtt tgg caa       637
Thr Ala Thr Gly Val Thr Val Ala Gly His Thr Trp Asn Val Trp Gln
        175                 180                 185 ggt cag caa acg agc tgg aag att att agc tac gtg ctg acc ccg ggt       685
Gly Gln Gln Thr Ser Trp Lys Ile Ile Ser Tyr Val Leu Thr Pro Gly
    190                 195                 200
```

```
gcc acc agc att agc aac ctg gat ctg aaa gcg att ctg gcc gac gcg      733
Ala Thr Ser Ile Ser Asn Leu Asp Leu Lys Ala Ile Leu Ala Asp Ala
205                 210                 215                 220 gct gct cgc ggc agc ctg aat acc tct gac tat ttg atc gat gtc gaa      781
Ala Ala Arg Gly Ser Leu Asn Thr Ser Asp Tyr Leu Ile Asp Val Glu
                225                 230                 235 gct ggt ttc gaa atc tgg caa ggc ggt caa ggt ctg ggt agc aac agc      829
Ala Gly Phe Glu Ile Trp Gln Gly Gly Gln Gly Leu Gly Ser Asn Ser
            240                 245                 250 ttt agc gtt tct gtc acg agc ggc act agc agc ccg act ccg acc cct      877
Phe Ser Val Ser Val Thr Ser Gly Thr Ser Ser Pro Thr Pro Thr Pro
        255                 260                 265 tct taa tga aggcatcaaa taaaacgaaa ggctcagtcg aaagactggg              926
Ser cctttcgttt tatctgttgt ttgtcggtga acgctctcct gagtaggaca aatccgccgg    986
gagcggattt gaacgttgcg aagcaacggc ccggagggtg gcgggcagga cgcccgccat   1046
aaactgccag gcatcaaatt aagcagaagg ccatcctgac ggatg                   1091

<210> SEQ ID NO 22
<211> LENGTH: 269
<212> TYPE: PRT
<213> ORGANISM: Artificial Sequence
<220> FEATURE:
<223> OTHER INFORMATION: Synthetic Construct

<400> SEQUENCE: 22

Met Ile Lys Val Pro Arg Phe Ile Cys Met Ile Ala Leu Thr Ser Ser
1               5                   10                  15

Val Leu Ala Ser Gly Leu Ser Gln Ser Val Ser Ala His Ala Thr Thr
            20                  25                  30

Ser Thr Cys Ser Pro Thr Ala Val Val Ser Val Ala Gly Asp Glu Tyr
        35                  40                  45

Arg Val Gln Ala Asn Glu Trp Asn Ser Ser Ala Gln Gln Cys Leu Thr
    50                  55                  60

Ile Asp Thr Ser Thr Gly Ala Trp Ser Val Ser Thr Ala Asn Phe Asn
65                  70                  75                  80

Leu Ala Thr Asn Gly Ala Pro Ala Thr Tyr Pro Ser Ile Tyr Lys Gly
                85                  90                  95

Cys His Trp Gly Asn Cys Thr Thr Ala Asn Val Gly Met Pro Ile Gln
            100                 105                 110

Val Ser Lys Ile Gly Ser Ala Val Thr Ser Trp Ser Thr Thr Gln Val
        115                 120                 125

Ser Ser Gly Ala Tyr Asp Val Ala Tyr Asp Ile Trp Thr Asn Ser Thr
    130                 135                 140

Pro Thr Thr Ser Gly Gln Pro Asn Gly Thr Glu Val Met Ile Trp Leu
145                 150                 155                 160

Asn Ser Arg Gly Gly Val Gln Pro Phe Gly Ser Gln Thr Ala Thr Gly
                165                 170                 175

Val Thr Val Ala Gly His Thr Trp Asn Val Trp Gln Gly Gln Gln Thr
            180                 185                 190

Ser Trp Lys Ile Ile Ser Tyr Val Leu Thr Pro Gly Ala Thr Ser Ile
        195                 200                 205

Ser Asn Leu Asp Leu Lys Ala Ile Leu Ala Asp Ala Ala Arg Gly
    210                 215                 220

Ser Leu Asn Thr Ser Asp Tyr Leu Ile Asp Val Glu Ala Gly Phe Glu
225                 230                 235                 240
```

-continued

```
Ile Trp Gln Gly Gly Gln Gly Leu Gly Ser Asn Ser Phe Ser Val Ser
            245                 250                 255

Val Thr Ser Gly Thr Ser Ser Pro Thr Pro Thr Pro Ser
            260                 265
```

EXTRACELLULAR SECRETION OF RECOMBINANT PROTEINS

CONTRACTUAL ORIGIN

The United States Government has rights in this invention under Contract No. DE-AC36-08G028308 between the United States Department of Energy and the Alliance for Sustainable Energy, LLC, the Manager and Operator of the National Renewable Energy Laboratory.

CROSS-REFERENCE TO RELATED APPLICATIONS

This application claims priority to U.S. Provisional Application No. 61/264,391, filed Nov. 25, 2009, the contents of which are incorporated by reference in their entirety.

REFERENCE TO SEQUENCE LISTING

This application contains a Sequence Listing submitted as an electronic text file entitled "09-53_Seq_ST25.txt," having a size in bytes of 70 kb and created on Nov. 10, 2009. Pursuant to 37 CFR §1.52(e)(5), the information contained in the above electronic file is hereby incorporated by reference in its entirety.

BACKGROUND

The biological conversion of cellulosic biomass to ethanol represents a major source of future energy, yet the current cost of converting biomass to fermentable sugars must be further reduced to render the process economically feasible. Most current strategies of ethanol production utilize simultaneous saccharification and fermentation (SSF) or simultaneous saccharification and co-fermentation (SSCF). The process configuration termed consolidated bioprocessing (CBP) would alleviate the financial strain of producing saccharolytic enzyme cocktails by combining all the necessary steps for ethanol production as an action of one organism.

One attractive candidate for a CBP organism is the gram-negative fermentative bacterium, *Zymomonas naobilis. Z. mobilis* has been studied for its high ethanol production rate, yield, and tolerance to the toxicity of the final product. In addition, *Z. mobilis* has the ability to ferment sugars at low pH, and has a naturally high tolerance to many of the inhibitory compounds found in lignocellulosic-derived hydrolysates. Furthermore, the use of the Entner-Doudoroff pathway allows *Z. mobilis* to achieve the near-theoretical maximum ethanol yields during fermentation while achieving relatively low biomass formation. Accordingly, *Z. mobilis* has been successfully used in SSF and SSCF processes. Additionally, *Z. mobilis* has been successfully engineered to ferment the pentose sugars, xylose and arabinose.

A necessary prerequisite to establishing an organism such as *Z. mobilis* as a CBP organism is to achieve high levels of cellulolytic enzyme expression. However, there is not yet a strong consensus on how to achieve maximal heterologous protein expression in *Z. mobilis*. Multiple groups have attempted heterologous expression of numerous genes including cellulolytic enzymes in *Z. mobilis* with varying degrees of success. The ability to achieve high levels of heterologous cellulase expression in CBP organisms such as *Z. mobilis* on a consistent basis needs further investigation.

While achieving high-level expression of cellulases is an important hurdle to clear in the development of a CBP organism, these enzymes must additionally be translocated to the extracellular media in order to come in contact with the substrate. One way to achieve this translocation is by harnessing the host-cell's secretion apparatus. However, there is very little knowledge of the capacity of *Z. mobilis* to secrete recombinant proteins.

The foregoing examples of the related art and limitations related therewith are intended to be illustrative and not exclusive. Other limitations of the related art will become apparent to those of skill in the art upon a reading of the specification and a study of the drawings.

SUMMARY

The following embodiments and aspects thereof are described and illustrated in conjunction with systems, tools and methods that are meant to be exemplary and illustrative, not limiting in scope. In various embodiments, one or more of the above-described problems have been reduced or eliminated, while other embodiments are directed to other improvements.

Exemplary embodiments provide isolated nucleic acid molecules encoding a polypeptide that functions as a secretion signal. The polypeptide may have the amino acid sequence of SEQ ID NO:2 or SEQ ID NO:4 or at least 95% identical to SEQ ID NO:2 or SEQ ID NO:4, while the isolated nucleic acid molecule may have the sequence of SEQ ID NO:1 or SEQ ID NO:3.

In certain embodiments, the nucleic acid molecule may be fused to an additional nucleic acid sequence encoding a polypeptide with cellulase activity. Examples include endoglucanases such as E1 or GH12 from *Acidothermus cellulolyticus*, or portions thereof. The fusion nucleic acid molecules may have the sequence of SEQ ID NO:5, SEQ ID NO:7, or SEQ ID NO:9; or may encode a polypeptide identical to (or at least 95% identical to) the amino acid sequence of SEQ ID NO:6, SEQ ID NO:8, or SEQ ID NO:10.

Exemplary embodiments further provide expression vectors including nucleic acid molecules described herein and host cells that express the vectors. In certain embodiments, the host cell is a microbial cell, such as a *Zymomonas* cell or a *Zymomonas mobilis* cell.

Also provided are recombinant polypeptides with the amino acid sequence of SEQ ID NO:2 or SEQ ID NO:4, or fusion polypeptides with the amino acid sequence of SEQ ID NO:2 or SEQ ID NO:4 fused to a protein with cellulase activity (e.g., endoglucanases such as E1 or GH12 from *A. cellulolyticus*). In some embodiments, the recombinant polypeptide may have the amino acid sequence of SEQ ID NO:6, SEQ ID NO:8, SEQ ID NO:10, or may be 95% identical to one of these amino acid sequences.

Exemplary embodiments also provide methods for producing a protein by culturing a host cell that expresses a recombinant polypeptide described herein and isolating the recombinant polypeptide. In some embodiments, the recombinant polypeptide comprises the amino acid sequence of SEQ ID NO:2 or SEQ ID NO:4 fused to a protein with cellulase activity. In certain embodiments, the recombinant polypeptide is secreted from the host cell and isolated from the culture media.

Additional embodiments provided methods for degrading lignocellulosic biomass by culturing the host cells described herein with the lignocellulosic biomass.

In addition to the exemplary aspects and embodiments described above, further aspects and embodiments will become apparent by reference to the drawings and by study of the following descriptions.

BRIEF DESCRIPTION OF THE DRAWINGS

Exemplary embodiments are illustrated in referenced figures of the drawings. It is intended that the embodiments and figures disclosed herein are to be considered illustrative rather than limiting.

FIG. 1 illustrates plasmid vectors, with relevant expression elements shown graphically. For E1 and GH12 plasmids, encoded amino acids are shown in parentheses.

DETAILED DESCRIPTION

Figure 2:
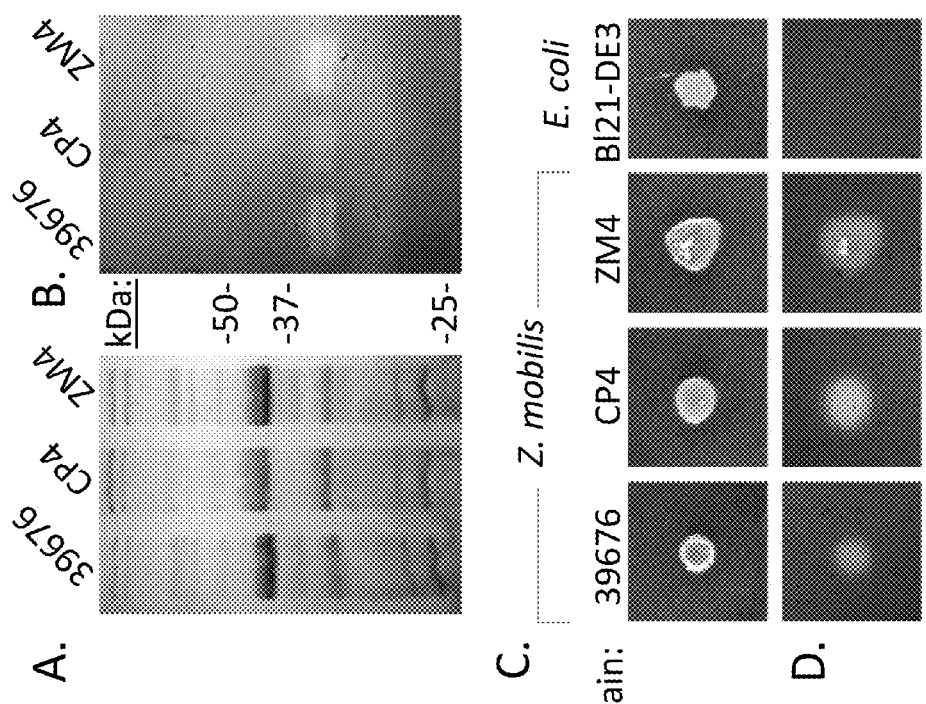
FIG. 2 shows the activity of the native cellulolytic proteins found in Z. mobilis strains. A) Coomassie stained polyacrylamide gel. B) carboxymethyl cellulose (CMC) zymogram. C) Patched colonies of Z. mobilis and E. coli growing on an RMG-CMC plate. D) Plate from "C" with cells removed and stained with Congo red to reveal areas of CMC degradation.

Nucleic acid sequences encoding polypeptides that function as secretion signals and their use in the production of recombinant proteins are disclosed herein. These secretion signals may be used to direct the secretion of recombinant proteins expressed in hosts such as Zymomonas mobilis, including cellulases, xylanases and other biomass degrading enzymes. For example, the sequences may be fused to the 5' end of genes encoding proteins such as the E1 endoglucanase from Acidothermus cellulolyticus, and thereby direct the extracellular secretion of active E1 protein in Z. mobilis cultures.

Two nucleic acid sequences derived from the genome of Z. mobilis strain ZM4, designated Z130 (SEQ ID NO:1) and Z331 (SEQ ID NO:3), have been found to function as strong secretion signals when fused to gene sequences. These signal sequences, when fused to gene sequences and expressed as a polypeptide, localize the resulting protein to the periplasm and extracellular space. As a result, proteins that were previously localized to the cytosol may be secreted from the cell and recovered from the extracellular media.

Without wishing to be bound by any particular theory, it is believed that the secretion signals utilize two separate pathways: the SecB-dependent pathway (Z130), and the Twin Arginine Translocation (TAT) pathway (Z331). One difference between the two pathways is that the SecB-dependent pathway transports the unfolded protein across the inner membrane in an ATP-dependent manner, while the TAT pathway transports the folded protein across the membrane in an ATP-independent manner using the proton motive force.

"Nucleic acid" or "polynucleotide" as used herein refers to purine- and pyrimidine-containing polymers of any length, either polyribonucleotides or polydeoxyribonucleotide or mixed polyribo-polydeoxyribonucleotides. This includes single- and double-stranded molecules (i.e., DNA-DNA, DNA-RNA and RNA-RNA hybrids) as well as "protein nucleic acids" (PNA) formed by conjugating bases to an amino acid backbone. This also includes nucleic acids containing modified bases.

Nucleic acids referred to herein as "isolated" are nucleic acids that have been removed from their natural milieu or separated away from the nucleic acids of the genomic DNA or cellular RNA of their source of origin (e.g., as it exists in cells or in a mixture of nucleic acids such as a library), and may have undergone further processing. Isolated nucleic acids include nucleic acids obtained by methods described herein, similar methods or other suitable methods, including essentially pure nucleic acids, nucleic acids produced by chemical synthesis, by combinations of biological and chemical methods, and recombinant nucleic acids that are isolated.

Nucleic acids referred to herein as "recombinant" are nucleic acids which have been produced by recombinant DNA methodology, including those nucleic acids that are generated by procedures that rely upon a method of artificial replication, such as the polymerase chain reaction (PCR) and/or cloning into a vector using restriction enzymes. Recombinant nucleic acids also include those that result from recombination events that occur through the natural mechanisms of cells, but are selected for after the introduction to the cells of nucleic acids designed to allow or make probable a desired recombination event. Portions of isolated nucleic acids that code for polypeptides having a certain function can be identified and isolated by, for example, the method disclosed in U.S. Pat. No. 4,952,501.

An isolated nucleic acid molecule can be isolated from its natural source or produced using recombinant DNA technology (e.g., polymerase chain reaction (PCR) amplification, cloning) or chemical synthesis. Isolated nucleic acid molecules can include, for example, genes, natural allelic variants of genes, coding regions or portions thereof, and coding and/or regulatory regions modified by nucleotide insertions, deletions, substitutions, and/or inversions in a manner such that the modifications do not substantially interfere with the nucleic acid molecule's ability to encode a polypeptide or to form stable hybrids under stringent conditions with natural gene isolates. An isolated nucleic acid molecule can include degeneracies. As used herein, nucleotide degeneracy refers to the phenomenon that one amino acid can be encoded by different nucleotide codons. Thus, the nucleic acid sequence of a nucleic acid molecule that encodes a protein or polypeptide can vary due to degeneracies.

A nucleic acid molecule is not required to encode a protein having protein activity. A nucleic acid molecule can encode a truncated, mutated or inactive protein, for example. In addition, nucleic acid molecules may also be useful as probes and primers for the identification, isolation and/or purification of other nucleic acid molecules, independent of a protein-encoding function.

Suitable nucleic acids include fragments or variants of SEQ ID NOS:1 and 3 that maintain the signal sequence function of Z130 and Z331. For example, a fragment can comprise the minimum nucleotides from SEQ ID NOS:1 and 3 required to encode a functional signal sequence. Nucleic acid variants include nucleic acids with one or more nucleotide additions, deletions, substitutions, including transitions and transversions, insertion, or modifications (e.g., via RNA or DNA analogs). Alterations may occur at the 5' or 3' terminal positions of the reference nucleotide sequence or anywhere between those terminal positions, interspersed either individually among the nucleotides in the reference sequence or in one or more contiguous groups within the reference sequence.

In certain embodiments, the nucleic acids are identical to the sequences represented as SEQ ID NO:1 or SEQ ID NO:3. In other embodiments, the nucleic acids may be least about 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO:1 or SEQ ID NO:3 and possess the signal sequence function of Z130 and Z331. Sequence identity calculations can be performed using computer programs, hybridization methods, or calculations. Exemplary computer program methods to determine identity and similarity between two sequences include, but are not limited to, the GCG program package, BLASTN, BLASTX, TBLASTX, and PASTA. The BLAST programs are publicly available from NCBI and other sources. For example, nucleotide sequence identity can be determined by comparing a query sequences to sequences in publicly available sequence databases (NCBI) using the BLASTN2 algorithm.

Embodiments of the nucleic acids include those that encode a polypeptide having the amino acid sequence of SEQ ID NO:2 and SEQ ID NO:4, or functional equivalents thereof. A functional equivalent includes fragments or variants that exhibit the ability to function as a signal sequence and direct the extracellular secretion of proteins. As a result of the degeneracy of the genetic code, many nucleic acid sequences can encode a polypeptide having the amino acid sequence of SEQ ID NO:2 and SEQ ID NO:4. Such functionally equivalent variants are contemplated herein.

Altered or variant nucleic acids can be produced by one of skill in the art using the sequence data illustrated herein and standard techniques known in the art. Variant nucleic acids may be detected and isolated by hybridization under high stringency conditions or moderate stringency conditions, for example, which are chosen to prevent hybridization of nucleic acids having non-complementary sequences. "Stringency conditions" for hybridizations is a term of art that refers to the conditions of temperature and buffer concentration that permit hybridization of a particular nucleic acid to another nucleic acid in which the first nucleic acid may be perfectly complementary to the second, or the first and second may share some degree of complementarity that is less than perfect. For example, conditions for nucleic acid hybridizations are explained in F. M. Ausubel et al. (eds), 1995, Current Protocols in Molecular Biology, John Wiley and Sons, Inc., New York, N.Y., the teachings of which are hereby incorporated by reference.

Nucleic acids may be derived from a variety of sources including DNA, cDNA, synthetic DNA, synthetic RNA, or combinations thereof. Such sequences may comprise genomic DNA, which may or may not include naturally occurring introns. Moreover, such genomic DNA may be obtained in association with promoter regions or poly (A) sequences. The sequences, genomic DNA, or cDNA may be obtained in any of several ways. Genomic DNA can be extracted and purified from suitable cells by means well known in the art. Alternatively, mRNA can be isolated from a cell and used to produce cDNA by reverse transcription or other means.

Oligonucleotides that are fragments of SEQ ID NOS: 1 and 3 and antisense nucleic acids that are complementary, in whole or in part, to SEQ ID NOS: 1 and 3 are contemplated herein. Oligonucleotides may be used as primers or probes or for any other use known in the art. Antisense nucleic acids may be used, for example, to inhibit gene expression when introduced into a cell or for any other use known in the art. Oligonucleotides and antisense nucleic acids can be produced by standard techniques known in the art.

Also disclosed herein are recombinant vectors, including expression vectors, containing the secretion signals Z130 and Z331. A "recombinant vector" is a nucleic acid molecule that is used as a tool for manipulating a nucleic acid sequence of choice or for introducing such a nucleic acid sequence into a host cell. A recombinant vector may be suitable for use in cloning, sequencing, or otherwise manipulating the nucleic acid sequence of choice, such as by expressing or delivering the nucleic acid sequence of choice into a host cell to form a recombinant cell. Such a vector typically contains heterologous nucleic acid sequences not naturally found adjacent to a nucleic acid sequence of choice, although the vector can also contain regulatory nucleic acid sequences (e.g., promoters, untranslated regions) that are naturally found adjacent to the nucleic acid sequences of choice or that are useful for expression of the nucleic acid molecules.

A recombinant vector can be either RNA or DNA, either prokaryotic or eukaryotic, and typically is a plasmid. The vector can be maintained as an extrachromosomal element (e.g., a plasmid) or it can be integrated into the chromosome of a recombinant host cell. The entire vector can remain in place within a host cell, or under certain conditions, the plasmid DNA can be deleted, leaving behind the nucleic acid molecule of choice. An integrated nucleic acid molecule can be under chromosomal promoter control, under native or plasmid promoter control, or under a combination of several promoter controls. Single or multiple copies of the nucleic acid molecule can be integrated into the chromosome. A recombinant vector can contain at least one selectable marker.

The term "expression vector" refers to a recombinant vector that is capable of directing the expression of a nucleic acid sequence that has been cloned into it after insertion into a host cell or other (e.g., cell-free) expression system. A nucleic acid sequence is "expressed" when it is transcribed to yield an mRNA sequence. In most cases, this transcript will be translated to yield an amino acid sequence. The cloned gene is usually placed under the control of (i.e., operably linked to) an expression control sequence. The phrase "operatively linked" refers to linking a nucleic acid molecule to an expression control sequence in a manner such that the molecule can be expressed when introduced (i.e., transformed, transduced, transfected, conjugated or conduced) into a host cell.

Recombinant vectors and expression vectors may contain one or more regulatory sequences or expression control sequences. Regulatory sequences broadly encompass expression control sequences (e.g., transcription control sequences or translation control sequences), as well as sequences that allow for vector replication in a host cell. Transcription control sequences are sequences that control the initiation, elongation, or termination of transcription. Suitable regulatory sequences include any sequence that can function in a host cell or organism into which the recombinant nucleic acid molecule is to be introduced, including those that control transcription initiation, such as promoter, enhancer, terminator, operator and repressor sequences. Additional regulatory sequences include translation regulatory sequences, origins of replication, and other regulatory sequences that are compatible with the recombinant cell (see, e.g., D. V. Goeddel, Methods Enzymol. 185:3-7). The expression vectors may contain elements that allow for constitutive expression or inducible expression of the protein or proteins of interest. For example, vectors comprising the Ptac promoter allow for constitutive expression in the absence of the lad gene, but expression may be induced by the addition of isopropyl-β-D-thiogalactopyranoside (IPTG) when the vector also contains the lad gene. Numerous inducible and constitutive expression systems are known in the art.

Typically, an expression vector includes at least one nucleic acid molecule encoding a sequence signal operatively linked to one or more expression control sequences (e.g., transcription control sequences or translation control sequences). In one aspect, an expression vector may comprise a nucleic acid encoding a secretion sequence, as described herein, fused to a nucleic acid encoding a protein to be expressed, and operably linked to at least one regulatory sequence. Exemplary embodiments include expression vectors comprising the nucleic acids encoding signal sequence Z130 fused to the catalytic domain (encoding amino acids 43-422) of the endoglucanase E1 from *A. cellulolyticus* (SEQ ID NO:5), the signal sequence Z331 fused to the catalytic domain of the endoglucanase E1 from *A. cellulolyticus* (SEQ ID NO:7), and the signal sequence Z130 fused to the catalytic domain (encoding amino acids 35-274) of the endoglucanase GH12 from *A. cellulolyticus* (SEQ ID NO:9). It should be understood that the design of the expression vector may depend on such factors as the choice of the host cell to be transformed and/or the type of polypeptide to be expressed.

Several regulatory elements (e.g., promoters and terminators) have been isolated and shown to be effective in the transcription and translation of heterologous proteins in the various hosts. Such regulatory regions, methods of isolation, manner of manipulation, etc. are known in the art. To obtain expression in eukaryotic cells, terminator sequences, polyadenylation sequences, and enhancer sequences that modulate gene expression may be required. Sequences that cause amplification of the gene may also be desirable. Suitable promoters include the Ptac, PBAD, PGAP, PEno or PPdc promoters, among others. Suitable terminators include the T1T2 and T7 terminators, among others.

Expression and recombinant vectors may contain a selectable marker, a gene encoding a protein necessary for survival or growth of a host cell transformed with the vector. The presence of this gene allows growth of only those host cells that express the vector when grown in the appropriate selective media. Typical selection genes encode proteins that confer resistance to antibiotics or other toxic substances, complement auxotrophic deficiencies, or supply critical nutrients not available from a particular media. Markers may be an inducible or non-inducible gene and will generally allow for positive selection. Non-limiting examples of selectable markers include the ampicillin resistance marker (i.e., beta-lactamase), tetracycline resistance marker, neomycin/kanamycin resistance marker (i.e., neomycin phosphotransferase), dihydrofolate reductase, glutamine synthetase, and the like. The choice of the proper selectable marker will depend on the host cell, and appropriate markers for different hosts as understood by those of skill in the art.

Suitable expression vectors may include (or may be derived from) plasmid vectors that are well known in the art, such as those commonly available from commercial sources. The Examples below illustrate the construction of exemplary expression vectors containing the signal sequences or signal sequences fused to polypeptides, as described herein. Vectors can contain one or more replication and inheritance systems for cloning or expression, one or more markers for selection in the host, and one or more expression cassettes. The inserted coding sequences can be synthesized by standard methods, isolated from natural sources, or prepared as hybrids. Ligation of the coding sequences to transcriptional regulatory elements or to other amino acid encoding sequences can be carried out using established methods. A large number of vectors, including bacterial, yeast, and mammalian vectors, have been described for replication and/or expression in various host cells or cell-free systems, and may be used with the secretion sequences described herein for simple cloning or protein expression.

Suitable expression vectors also include pZB188, pFlag-CTC, or p25143 or other vectors comprising the Ptac, PBAD, PGAP, PEno or PPdc promoters. Examples of expression vectors containing the signal sequences are described below and include pJL111, pJL112, and pJL113. In certain embodiments, an expression vector may include an expression cassette comprising a promoter, secretion signal, gene (e.g., encoding a cellulase or fragment thereof) and terminator sequence. Examples include the Ptac-Z130-E1-T1T2 cassette represented as SEQ ID NO: 17, the Ptac-Z331-E1-T1T2 cassette represented as SEQ ID NO: 19, or the Ptac-Z130-GH12-T1T2 cassette represented as SEQ ID NO:21.

It will be appreciated by one skilled in the art that use of recombinant DNA technologies can improve control of expression of transformed nucleic acid molecules by manipulating, for example, the number of copies of the nucleic acid molecules within the host cell, the efficiency with which those nucleic acid molecules are transcribed, the efficiency with which the resultant transcripts are translated, and the efficiency of post-translational modifications. Additionally, the promoter sequence might be genetically engineered to improve the level of expression as compared to the native promoter. Recombinant techniques useful for controlling the expression of nucleic acid molecules include, but are not limited to, integration of the nucleic acid molecules into one or more host cell chromosomes, addition of vector stability sequences to plasmids, substitutions or modifications of transcription control signals (e.g., promoters, operators, enhancers), substitutions or modifications of translational control signals (e.g., ribosome binding sites), modification of nucleic acid molecules to correspond to the codon usage of the host cell and deletion of sequences that destabilize transcripts.

The nucleic acids, including parts or all of expression vectors, may be isolated directly from cells, or, alternatively, the polymerase chain reaction (PCR) method can be used to produce the nucleic acids. Primers used for PCR can be synthesized using the sequence information provided herein and can further be designed to introduce appropriate new restriction sites, if desirable, to facilitate incorporation into a given vector for recombinant expression. The nucleic acids can be produced in large quantities by replication in a suitable host cell (e.g., prokaryotic or eukaryotic cells such as bacteria, yeast, insect or mammalian cells). The production and purification of nucleic acids are described, for example, in Sambrook et al., 1989; F. M. Ausubel et al., 1992, Current Protocols in Molecular Biology, J. Wiley and Sons, New York, N.Y.

The nucleic acids described herein may be used in methods for production of proteins or polypeptides through incorporation into cells, tissues, or organisms. In some embodiments, a nucleic acid encoding all or part of Z130 (SEQ ID NO:2) or Z331 (SEQ ID NO:4) or a functional fragment thereof, or a fusion such as those represented by SEQ ID NOS: 5, 7, or 9, may be incorporated into a vector for expression of the encoded polypeptide in suitable host cells. The vector may then be introduced into one or more host cells by any method known in the art. One method to produce an encoded protein includes transforming a host cell with one or more recombinant nucleic acids (such as expression vectors) to form a recombinant cell. The term "transformation" is generally used herein to refer to any method by which an exogenous nucleic acid molecule (i.e., a recombinant nucleic acid molecule) can be inserted into a cell, but can be used interchangeably with the term "transfection."

Non-limiting examples of suitable host cells include bacteria, archea, insect, fungi (e.g., yeast), plant, and animal cells (e.g., mammalian). Specific examples include *Zymomonas mobilis, Escherichia coli, Bacillus subtilis, Saccharomyces cerevisiae*, SF9 cells, C129 cells, 293 cells, Neurospora, and immortalized mammalian myeloid and lymphoid cell lines, VERO and HeLa cells, CHO cells, and W138, BHK, and COS cell lines. Cell-free expression systems known in the art may also be suitable. Host cells can be either untransfected cells or cells that are already transfected with at least one other recombinant nucleic acid molecule.

In exemplary embodiments, the host cell may be a microbial cell, such as a bacterial cell. The host cell may be from the genus *Zymomonas* or from a strain of *Z. mobilis* such as *Z. mobilis* strains 39676, CP4, or ZM4. *Z. mobilis* has proven to be an extremely valuable organism in the conversion of biomass-derived sugars to ethanol. In addition to its fermentative abilities, *Z. mobilis* cells expressing the nucleic acids described herein may also play a significant role in the degradation of lignocellulosic biomass. Given the proven adeptness of *Z. mobilis* in industrial-scale fermentation, the ability to express high levels of active cellulases, and the capacity to secrete these enzymes as shown herein, *Z. mobilis* may be suitable as a CBP organism.

Suitable *Zymomonas* host cells include cells previously transformed with additional expression vectors containing genes useful in the degradation of biomass or the fermentation of sugars into ethanol and other industrial chemicals. Examples include *Zymomonas* cells capable of utilizing pentose sugars such as xylose or arabinose as a carbon source, as described, for example in U.S. Pat. Nos. 5,514,583; 5,843,760; 6,566,107; and 7,223,575.

Host cells can be transformed, transfected, or infected as appropriate by any suitable method including electroporation, calcium chloride-, lithium chloride-, lithium acetate/polyethylene glycol-, calcium phosphate-, DEAE-dextran-, liposome-mediated DNA uptake, spheroplasting, injection, microinjection, microprojectile bombardment, phage infection, viral infection, or other established methods. Alternatively, vectors containing the nucleic acids of interest can be transcribed in vitro, and the resulting RNA introduced into the host cell by well-known methods, for example, by injection (see, Kubo et al., FEBS Letts. 241:119). Exemplary embodiments include a host cell or population of cells expressing one or more nucleic acid molecules or expression vectors described herein (for example, a genetically modified microorganism). The cells into which nucleic acids have been introduced as described above also include the progeny of such cells.

Host cells carrying an expression vector (i.e., transformants or clones) may be selected using markers depending on the mode of the vector construction. The marker may be on the same or a different DNA molecule. In prokaryotic hosts, the transformant may be selected, for example, by resistance to ampicillin, tetracycline or other antibiotics. Production of a particular product based on temperature sensitivity may also serve as an appropriate marker.

Host cells may be cultured in an appropriate fermentation medium. An appropriate, or effective, fermentation medium refers to any medium in which a host cell, including a genetically modified microorganism, when cultured, is capable of expressing polypeptides or of catalyzing the production of sugars from lignocellulosic biomass. Such a medium is typically an aqueous medium comprising assimilable carbon, nitrogen and phosphate sources, but can also include appropriate salts, minerals, metals and other nutrients. Microorganisms and other cells can be cultured in conventional fermentation bioreactors and by any fermentation process, including batch, fed-batch, cell recycle, and continuous fermentation. The pH of the fermentation medium is regulated to a pH suitable for growth and protein production of the particular organism. The fermentor can be aerated in order to supply the oxygen necessary for fermentation and to avoid the excessive accumulation of carbon dioxide produced by fermentation. Culture media and conditions for various host cells are known in the art. Exemplary conditions for the culture of bacteria such as *Z. mobilis* can be found in the Examples that follow and in Senthilkumar et al., Arch. Microbiol. 191:529-41 and Arfman et al., J. Bacteriol. 174:7370-8.

The nucleic acid signal sequences described herein encode polypeptides with the amino acid sequences represented by SEQ ID NO:2 (Z130) and SEQ ID NO:4 (Z331). As used herein, the terms "protein" and "polypeptide" are synonymous. "Peptides" are defined as fragments or portions of polypeptides, preferably fragments or portions having at least one functional activity as the complete polypeptide sequence. "Isolate" proteins or polypeptides are proteins or polypeptides purified to a state beyond that in which they exist in cells. In certain embodiments, they may be at least 10% pure; in others, they may be substantially purified to 80% or 90% purity or greater. Isolated proteins or polypeptides include essentially pure proteins or polypeptides, proteins or polypeptides produced by chemical synthesis or by combinations of biological and chemical methods, and recombinant proteins or polypeptides that are isolated. Proteins or polypeptides referred to herein as "recombinant" are proteins or polypeptides produced by the expression of recombinant nucleic acids.

Proteins or polypeptides encoded by nucleic acids as well as functional portions or variants thereof are also described herein. Polypeptide sequences may be identical to the amino acid sequence of SEQ ID NO:2 or SEQ ID NO:4, or may include up to a certain integer number of amino acid alterations. Such protein or polypeptide variants retain functionality as signal sequences, and include mutants differing by the addition, deletion or substitution of one or more amino acid residues, or modified polypeptides and mutants comprising one or more modified residues. The variant may have one or more conservative changes, wherein a substituted amino acid has similar structural or chemical properties (e.g., replacement of leucine with isoleucine). Alterations may occur at the amino- or carboxy-terminal positions of the reference polypeptide sequence or anywhere between those terminal positions, interspersed either individually among the amino acids in the reference sequence or in one or more contiguous groups within the reference sequence.

In certain embodiments, the polyptides may be at least about 80%, 81%, 82%, 83%, 84%, 85%, 86%, 87%, 88%, 89%, 90%, 91%, 92%, 93%, 94%, 95%, 96%, 97%, 98% or 99%, identical to SEQ ID NO:2 or SEQ ID NO:4 and possess signal sequence function. Percent sequence identity can be calculated using computer programs (such as the BLASTP and TBLASTN programs publicly available from NCBI and other sources) or direct sequence comparison. Polypeptide variants can be produced using techniques known in the art including direct modifications to isolated polypeptides, direct synthesis, or modifications to the nucleic acid sequence encoding the polypeptide using, for example, recombinant DNA techniques.

Modified polypeptides, including those with post-translational modifications, are also contemplated herein. Isolated polypeptides may be modified by, for example, phosphorylation, methylation, farnesylation, carboxymethylation, geranyl geranylation, glycosylation, acetylation, myristoylation, prenylation, palmitation, amidation, sulfation, acylation, or other protein modifications. They may also be modified with a label capable of providing a detectable signal, either directly or indirectly, including, but not limited to, radioisotopes and fluorescent compounds. The polypeptides may be useful as antigens for preparing antibodies by standard methods. Monoclonal and polyclonal antibodies that specifically recognize the polypeptides disclosed herein are contemplated.

The signal sequences represented by SEQ ID NO:2 and SEQ ID NO:4 may be expressed, isolated and used as stand-alone polypeptides. These signal sequences may also be fused to one or more additional polypeptides (using, for example, recombinant technology) to direct the secretion of the polypeptide from a host cell. In this context, the additional polypeptide is referred to as the "secreted polypeptide," and may include a complete polypeptide or a functional domain of a polypeptide. Any protein desired to be secreted from a host cell (e.g., an enzyme or pharmaceutically active protein, etc.) is suitable for use with the signal sequences described herein. Signal sequences are typically fused to the amino terminus of a secreted polypeptide, but can be joined to the carboxyl terminus of the secreted protein. Fused polypeptides may be produced by culturing a recombinant cell transfected with a fusion nucleic acid molecule that encodes a signal sequence attached to either the carboxyl or amino terminal end of the secreted polypeptide or domain thereof. In certain embodiments, the fused signal sequence may also increase the expression of the secreted polypeptide in addition to directing its secretion.

While the signal sequences and expression systems disclosed herein may be applied to any gene/protein, they are well suited for the expression and secretion of cellulolytic enzymes. In order to effectively break down lignocellulosic biomass using a CBP organism, several classes of cellulolytic enzymes will likely need to be co-expressed in the organism. For example, the simultaneous expression of an endoglucanase, an exoglucanase, and a β-glucosidase may be needed for optimal biomass break down. The Examples below demonstrate the effective production and secretion of two endo-1,4-β-glucanases. In one of these illustrative embodiments, the signal sequences Z130 and Z331 were fused to the 5' end of the catalytic domain of the E1 gene from *A. cellulolyticus*, and were shown to direct the secretion of active E1 enzyme into the extracellular space.

Suitable secreted polypeptides include enzymes with the ability to degrade carbohydrate-containing materials, such as cellulases with endoglucanase activity, exoglucanase activity, or β-glucosidase activity, or hemicellulases with endoxylanase activity, exoxylanase activity, or β-xylosidase activity. Further examples of suitable secreted polypeptides include enzymes that possess cellobiohydrolase, α-glucosidase, xylanase, β-xylosidase, α-galactosidase, β-galactosidase, α-amylase, glucoamylases, arabinofuranosidase, mannanase, β-mannosidase, pectinase, acetyl xylan esterase, acetyl mannan esterase, ferulic acid esterase, coumaric acid esterase, pectin methyl esterase, laminarinase, xyloglucanase, galactanase, glucoamylase, pectate lyase, chitinase, exo-β-D-glucosaminidase, cellobiose dehydrogenase, ligninase, amylase, glucuronidase, ferulic acid esterase, pectin methyl esterase, arabinase, lipase, glucosidase or glucomannanase activities. In general, glycoside hydrolases may be used as secreted polypeptides.

The secreted polypeptide may itself be a fusion protein that includes one or more fusion segments, which may be heterologous in sequence to the protein sequence (i.e., different than protein sequence). Suitable fusion segments include segments that can enhance a protein's stability, provide other desirable biological activity, or assist with the purification of the protein (e.g., by affinity chromatography). A suitable fusion segment can be a domain of any size that has the desired function (e.g., imparts increased stability, solubility, action or biological activity; or simplifies purification of a protein).

The expression and secretion of two cellulolytic enzymes (E1 and GH12) in *E. coli* or *Z. mobilis* are shown in the Examples that follow. E1 (locus tag: Acel_0614) and GH12 (locus tag: Acel_0619) are both from the acidothermophile *A. cellulolyticus* and are representative of families 5 and 12 glycoside hydrolases, respectively (see, U.S. Pat. Nos. 5,536, 655 and 7,059,993). E1 is an endo-1,4-β-glucanase, and GH12 is a protein that exhibits very high sequence identity to the GH12 domain of GuxA (Acel_0615) from *A. cellulolyticus*. GuxA has activities against a wide variety of substrates including carboxymethyl cellulose arabinoxylan, xylan and xyloglucan. Homology modeling suggests that GH12 and the GH12 domain of GuxA most closely resemble an endo-1,4-β-glucanase. In certain embodiments, the secreted polypeptide may be full-length proteins such as E1 or GH12 (described, for example, in Baker et al., Applied Biochemistry and Biotechnology 45-6:245-256 and U.S. Pat. No. 7,059,993). In other embodiments, the secreted polypeptide may be a functional domain of a polypeptide, such as the catalytic domain. Examples include the catalytic domains of E1 and GH12. The nucleic acid sequences encoding the catalytic domain of E1 (amino acids 43-422) and the catalytic domain of GH12 (amino acids 35-274) are represented by SEQ ID NO: 11 and SEQ ID NO:13, respectively. Secreted polypeptides may be subjected to codon optimization to enhance heterologous expression in host cells such as Z. mobilis.

The extracellular presence of secreted proteins may be detected by any assay known in the art to detect a protein of interest. Examples include enzymatic activity assays, detection with specific antibodies (immunoblotting, ELISA, etc.), and other suitable detection techniques. For example, the extracellular presence of E1 from A. cellulolyticus may be demonstrated by showing degradation of carboxymethyl cellulose and hydrolysis of methylumbelliferyl cellobioside (MUC) or by immunoblotting using an E1-specific antibody.

Secreted polypeptides may also be isolated or recovered from the media used in host cell cultures or cell-free expression systems. The phrase "recovering the protein" refers to collecting the whole culture medium containing the protein and need not imply additional steps of separation or purification. Proteins can be purified using a variety of standard protein purification techniques, such as affinity chromatography, ion exchange chromatography, filtration, electrophoresis, hydrophobic interaction chromatography, gel filtration chromatography, reverse phase chromatography, concanavalin A chromatography, chromatofocusing, differential solubilization, preparative disc-gel electrophoresis, isoelectric focusing, HPLC, reversed-phase HPLC, or countercurrent distribution. The polypeptide may contain an additional protein or epitope tag that facilitates detection or purification, such as c-myc, haemagglutinin (HA), polyhistidine, GLU-GLU, FLAG-tag, glutathione-S-transferase (GST), green fluorescent protein (GFP), or maltose binding protein (MBP). Such tags may be removed following the recovery of the polypeptide.

Polypeptides may be retrieved, obtained, or used in "substantially pure" form, a purity that allows for the effective use of the protein in any method described herein or known in the art. For a protein to be useful in any of the methods described herein or in any method utilizing enzymes of the types described herein, it is substantially free of contaminants, other proteins and/or chemicals that might interfere or that would interfere with its use in the method (e.g., that might interfere with enzyme activity), or that at least would be undesirable for inclusion with a protein.

Methods for breaking down lignocellulose and lignocellulose-containing biomass are also disclosed herein. Host cells transformed with the nucleic acids and expression vectors described herein may be brought into contact with a lignocellulose-containing biomass (for example, by culturing the host cell in the presence of the lignocellulose-containing biomass) to result in its degradation. Treated biomass is typically degraded into simpler forms of carbohydrates, and in some cases glucose, which may then used in the formation of ethanol or other industrial chemicals, as is known in the art. Biomass degradation may be achieved by culturing the host cell in media supplemented with a source of lignocellulose-containing biomass, in addition to media components necessary for growth of the host cell. In addition to the use of lignocellulose-containing biomass as an energy source for the host, the growth media may need to be supplemented with additional components including, but not limited to, yeast extract. Multiple enzymes may need to be expressed and secreted by one or more host cells in order to utilize lignocellulose-containing biomass as a primary source of energy. Such enzymes may be expressed by one or more host cells, or purified enzymes or mixtures of enzymes may be directly added to the culture. For example, endoglucanase, exoglucanase, and β-glucosidase activities may be required to fully degrade cellulosic materials into fermentable sugars. These enzymatic activities can arise from individual enzymes, or in some cases, multiple types of cellulolytic activity can arise from the same enzyme. Further, there are different enzymatic activities that can substitute for other activities. For instance, processive endoglucanases can have overlapping roles with exoglucanases.

Lignocellulose-containing biomass may be derived from any source known in the art. Examples include bioenergy crops, agricultural residues, municipal solid waste, industrial solid waste, sludge from paper manufacture, yard waste, wood and forestry waste. Examples of biomass include, but are not limited to, corn grain, corn cobs, crop residues such as corn husks, corn stover, corn fiber, grasses, wheat, wheat straw, barley, barley straw, hay, rice straw, switchgrass, waste paper, sugar cane bagasse, sorghum, soy, components obtained from milling of grains, trees, branches, roots, leaves, wood (e.g., poplar) chips, sawdust, shrubs and bushes, vegetables, fruits, flowers and animal manure. Biomass samples may be processed or pretreated using known methods prior to or after degradation. Examples of pretreatment methods can be found, for example, in Galbe et al., Adv Biochem Eng Biotechnol; 108:41-65.

In certain embodiments, the host cell used to degrade the lignocellulose-containing biomass may be a strain of Z. mobilis. The results presented in the Examples below demonstrate that some Z. mobilis strains (e.g., 39676, CP4 and ZM4) may natively produce an endogenous activity against carboxymethyl cellulose (CMC), and that this activity can be detected extracellularly. Further, the results demonstrate that Z. mobilis can achieve GH12 expression levels approaching 5% of the total cellular protein (in a largely soluble and enzymatically active form), and this level of expression was sustained and stable throughout the entire logarithmic phase of growth. Z. mobilis capable of handling high levels of additional protein expression, including the high level, constitutive expression of cellulolytic enzymes, before major growth rate limitations occur. The results also demonstrate that Z. mobils is capable of translocating both E1 and GH12 (nearly 50% and 40% of the respective protein) to the periplasmic space or the extracellular media when the genes encoding these cellulases are fused with the secretion signals Z130 and Z331. The combination of these traits, along with the demonstrated ability of Z. mobils strains to ferment a variety of sugars to ethanol, make Z. mobilis attractive as a CBP organism.

EXAMPLES

Example 1

The following materials and methods were used in subsequent Examples detailed below.
Strains, Media and Growth Conditions
Z. mobilis strains 39676 (ATCC), ZM4 and CP4 were grown in RMG media (w/v 1% yeast extract, 0.2% $KH_2PO_4$, 2% glucose, and for plates: 1.5% Bactoagar) at 30° C. and shaken at 120 RPM. Where applicable, tetracycline was added to a final concentration of 20 µg/mL for plates, and 10 µg/mL for liquid culture.

Z. mobilis Transformations

Transformations of Z. mobilis used standard electroporation techniques with the following conditions: 200Ω25 µF, and 1.6 kV using a Biorad Gene Pulser.

Gene Synthesis and Codon Optimization

The coding sequences of the catalytic domains of E1 and GH12 from A. cellulolyticus were codon optimized based on the codon bias of Z. mobilis strain ZM4, and synthesized by DNA 2.0 (Menlo Park, Calif.).

Plasmids

Schematics of all plasmids used in this study are shown in FIG. 1. Using standard overlap PCR techniques, the gap promoter region from Z. mobils genomic DNA (ATCC strain 39676) was fused to the T7 terminator region from plasmid pET101/D-topo (Invitrogen, Carlsbad Calif.) separated by a NotI restriction site to create plasmid pJL100.

To create plasmids pJL101 and pJL103, PCR products representing coding sequences for E1 and GH12 were cloned into pFLAG-CTC (Sigma-Aldrich, St. Louis, Mo.). A. cellulolyticus genomic DNA was used as the PCR template for the E1 and GH12 coding sequences for plasmids pJL101 and pJL103. pJL101 encodes for the first 274 amino acid residues of GH12 while pJL103 encodes for amino acid residues 42-404 of E1.

Plasmids p25143 and p25144 were codon-optimized, synthesized, and sub-cloned by DNA 2.0 (Menlo Park, Calif.) and encode the amino acid residues 42-422 of E1 and amino acid residues 35-274 of GH12. These sequences were then subcloned into the NotI site of vector pZB188 (see Zhang et al., Abstracts of Papers of the American Chemical Society 209:115-BTEC) to create plasmids p25143 and p25144, respectively.

Plasmid pJL110 was created by PCR amplifying the Z. mobilis strain 39676 pdc gene including extended 5' and 3' non-coding sequences with flanking NotI sequences incorporated. This PCR product was Topo-cloned into pYES2.1 (Invitrogen, Carlsbad, Calif.) to create plasmid pYes2.1-PDC. The E1 PCR product was amplified and homology to the 5' and 3' non-coding sequences of Z. mobilis pdc was incorporated on the ends of the PCR product Saccharomyces cerevisiae strain w303 was transformed with this PCR product as well as KpnI-linearized pYES2.1-E1. Through endogenous homologous recombination in yeast, the Z. mobilis pdc ORF was exchanged with the E1 ORF on plasmid pYes2.1-E 1 to create plasmid pYES2.1-PDC-E1-PDC. The E1 fragment containing the 5' and 3' sequences of pdc was excised with NotI and ligated into pZB188 to create plasmid pJL110.

To create plasmids pJL111 and pJL113 the sequence (ZM0130, ATGATAAAAGTCCCGCGGTTCATCTG-TATGATCGCGCTTACATCCAGCGT TCTGGCAAGCG-GCCTTTCTCAAAGCGTTTCAGCTCAT; SEQ ID NO:1) was fused to the 5' termini of E1 and GH12 genes respectively. For plasmid pJL112, the predicted secretion signal of the predicted Z. mobilis ORF ZM0331(ATGAAAA-GAAAGCTTGGTCGTCGCCAGTTAT-
TAACTGGCTTTGT TGCCCTTGGCGGTATGGCGAT-TACAGCTGGTAAGGCGCAGGCTTCT; SEQ ID NO:3) was fused to the 5' terminus of the E1 gene sequence.

Western Blots and CMC Zymogram Analysis

Following SDS-PAGE, cellular proteins were transferred to a polyvinylidene fluoride (PVDF) membrane at a constant 200V for one hour. A mouse monoclonal E1-specific antibody diluted 1:4000 in 3% milk in Tris-Buffered Saline Tween-20 TBST was added to the PVDF membranes and allowed to incubate for 2 hours at room temperature. After washing the membranes with TBST they were incubated in TBST containing 3% milk and a goat-anti-mouse alkaline phosphatase conjugated secondary antibody (diluted 1:4000) for 1 hour at room temperature. The protocol used to perform the carboxymethyl cellulose (CMC) zymograms is described in Taylor et al., J Bacteriol 188(11):3849-61, except the reaction buffer used was 50 mM sodium citrate buffer pH 7.0.

Total and Extracellular Fraction Preparations

For each strain an equal volume of cell culture was moved into two separate microcentrifuge tubes. In one of the replicates, the cells were removed by two rounds of centrifugation (5 minutes, 15000×G each) to create the extracellular fraction. Equal volumes of the culture with cells (Total) and the extracellular fraction were treated with 10× BugBuster lysis buffer (Novagen) to create a 1× concentration of lysis buffer. Samples were vortexed and incubated at room temperature for 20 minutes. Samples were centrifuged (5 minutes, 15000× G) and the supernatants were moved to a new tube.

Subcellular Fractionations 50 mL cultures of Z. mobilis were grown to saturation, and then centrifuged at 4000×G for 10 minutes. Cells were resuspended in periplasting buffer (200 mM TRIS-HCL PH 7.5, 20% Sucrose, 1 mM EDTA, and 2.5 million units of Lysozyme (0.00625 g/5 mL; Sigma L-6876) at a volume corresponding to 4 mL/g of wet weight of the cell pellet. Multiple periplasting times were tested empirically to find the longest time point where no more than 5% of the ADH activity was found within the periplasmic fraction (Typically 5 minutes; ADH assay detailed below). This was to ensure maximal release of periplasmic contents, while minimizing contamination with cytoplasmic contents.

Following the incubation in periplasting buffer, ice-cold $H_2O$ was added at a volume corresponding to 6 mL/g of wet weight of the original cell pellet. Cells were incubated on ice for 10 minutes, and then centrifuged at 4° C. for 10 minutes at 4000×G. Periplasmic fraction was transferred to a new tube, and then BugBuster HT lysis buffer (Novagen) was added to the cell pellet at a volume corresponding to 10 mL/g wet weight of the original cell pellet. This lysing reaction was incubated for 20 minutes at room temperature and centrifuged for 5 minutes at 15000×G. The supernatant represents the cytoplasmic fraction.

E1 and GH12 Activity Assays

10 µL of protein lysates (whole cell lysates, periplasmic and cytoplasmic fractions) were added to 90 µL of reaction buffer [50 mM sodium citrate, PH 7.0, and 0.00125 g/5 mL 4-methylumbelliferyl β-D-cellobiopyranoside (Sigma Aldrich)] in a 96-well microtiter plate. Reactions were incubated at 50° C. for 30 minutes, and analyzed for fluorescence using a BMG Labtech FLUOstar Omega with an excitation of 355 nm and an emission of 460 nm.

ADH Assays

44 µL of 50 mM sodium pyrophosphate, pH 8.8 was added to a 96-well microtiter plate, followed by 2 µL of either periplasmic or cytoplasmic fractions, 50.6 µL of 15 mM β-nicotinamide adenine dinucleotide hydrate (Sigma N7004) and 3.4 µL 95% ethanol were added to the wells, and then the absorbance at 340 nm was measured immediately and subsequently every 2 minutes for 14 minutes using a BMG Labtech FLUOstar Omega. The $\Delta A_{340\,nm}$ was calculated and the relative contribution of the periplasmic and cytoplasmic fraction to the total rate was calculated to determine the percent localization of ADH activity.

Example 2

During the process of investigating protein lysates of Z. mobilis for carboxymethyl cellulose (CMC) activity, we discovered that the *Z. mobilis* strains used in this study (i.e., 39676, ZM4, and CP4) demonstrate activity against CMC. This activity manifested itself as two, closely spaced, yet distinct molecular weight bands (FIG. 2A, B). The apparent size of these bands (FIG. 2B) is consistent with the predicted molecular weight of the CelA protein (37 kDa), suggesting that one or both of the bands may represent CelA. The larger of the two bands may represent the full length CelA, and the smaller band may represent the mature protein with the signal peptide removed. Subcellular fractionation experiments detailed later in this study (FIG. 7B) show that the larger of the two bands is the only band present in the cytoplasmic fraction, while both forms are present in the periplasmic fraction. As signal peptides are typically removed in the periplasm, this would be expected if in fact the two bands represented the full length protein and the mature protein. We further observed that cellulolytic activity against CMC can also be detected extracellularly (FIG. 2 C, D). These finding are consistent with CelA containing a predicted secretion signal at the N-terminus. The finding that *Z. mobilis* naturally expresses and secretes at least one endogenous cellulase provides support that *Z. mobilis* might prove adept at expressing and secreting heterologous cellulases. Based on this finding, we chose to examine the heterologous expression and secretion of multiple cellulolytic enzymes in *Z. mobilis*.

Example 3

Figure 3:
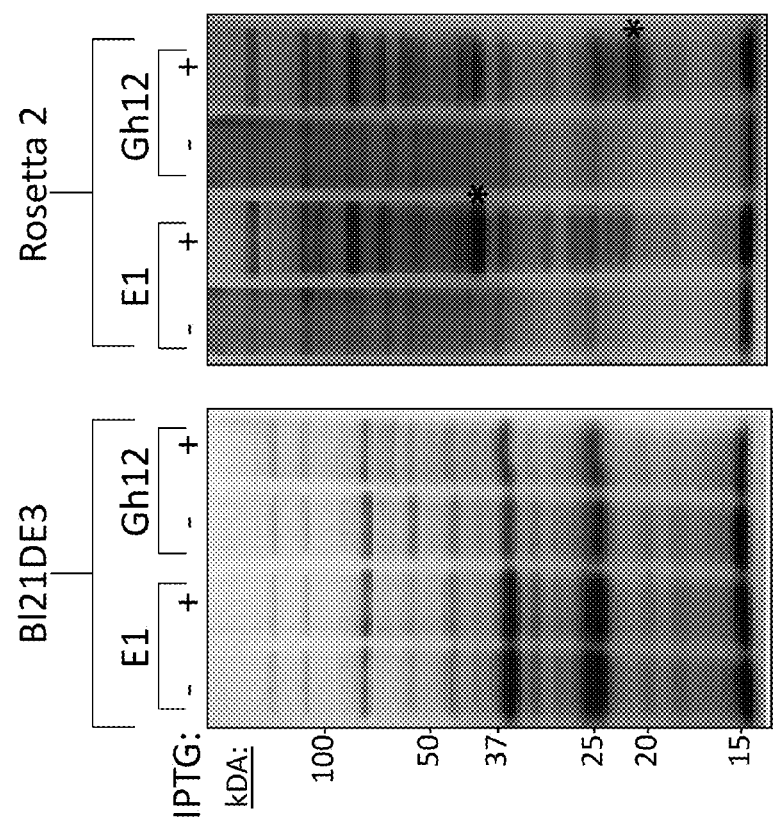
FIG. 3 shows the expression of E1 and GH12 in E. coli strains B121-DE3 and Rosetta 2, as demonstrated by Coomassie stained polyacrylamide gel of protein lysates from E. coli strains BL21-DE3 and Rosetta 2 harboring plasmids pJL101 ("E1"), and pJL103 ("GH12") with (+) or without (–) protein induction with 1 mM IPTG.

We investigated whether the altered codon bias between *A. cellulolyticus* and *Z. mobilis* would hinder successful expression of E1 and GH12 in *Z. mobilis*. As there are no commercially available codon-enhanced strains of *Z. mobilis*, we chose to preliminarily address this question using *E. coli* as our expression host, using a codon-enhanced strain of *E. coli*. Separate plasmids containing Ptac-driven genes encoding the E1 and GH12 endoglucanases (Acel-0614 and Acel-0619, respectively) from *A. cellulolyticus*. FIG. 3 shows that while expression of E1, and GH12 was not detected upon IPTG induction in BL21-DE3 cells, all three were strongly induced in the codon enhanced Rosetta2 strain of *E. coli* (EMD; Madison, Wis.). This data strongly suggests that the differential codon bias between the host organism (*A. cellulolyticus*) and the expression organism (*E. coli*) could be a major barrier to heterologous expression in *E. coli*. By inference, this may also suggest that differential codon usage between *A. cellulolyticus* and *Z. mobilis* may have a detrimental effect on the expression of E1 and GH12 in *Z. mobilis*.

To test the effect that differential codon bias might having on gene expression, the gene sequence encoding the E1 catalytic domain was codon optimized for *Z. mobilis* and the synthesized gene was tested for its expression in *Z. mobilis* (DNA 2.0; Menlo Park, Calif.). The expression of the native and codon-optimized (version "E1-c/o") gene sequence of the E1 catalytic domain ("E1") was examined in multiple strains of *Z. mobilis*. Both constructs were expressed nearly equally as well in *Z. mobilis*, though the native E1 may have been expressed slightly better than E1-c/o (FIGS. 4B and 4C). The fact that the codon-optimized version of E1 did not express significantly better than the native E1 coding sequence suggests that either the codon optimization strategy undertaken was suboptimal, or that differential codon usage bias was not a major obstacle (or at least not the sole obstacle) to achieving higher levels of expression.

Figure 4:
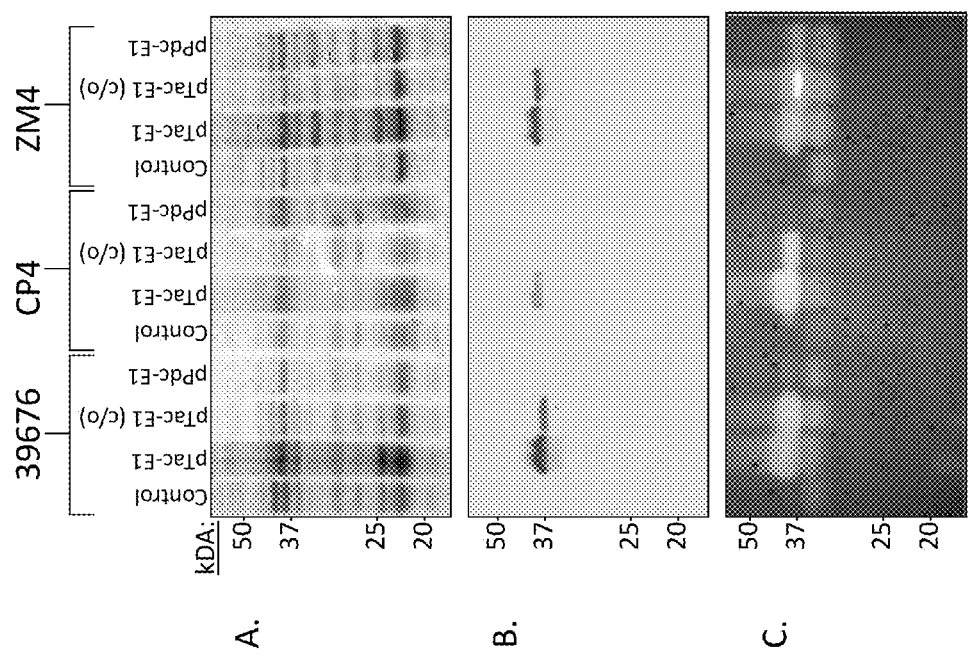
FIG. 4 shows the expression of various E1 constructs in multiple strains of Z. mobilis: Protein lysates from Z. mobilis strains 39676, CP4, and ZM4 transformed with the plasmids pZB188 ("control"), pJL108 ("pTac-E1"), p25143 ["pTac-E1 (c/o)], and pJL110 ("pPdc-E1") were run identically on two independent 12% polyacrylamide gels supplemented with 0.12% carboxymethyl cellulose (CMC). A) A PVDF membrane stained with amido black to show total protein. B) Immunoblot probed with an α-E1 antibody. C) A CMC zymogram performed on the second of two duplicate polyacrylamide gels to show cellulolytic activity. E1 activity is represented by the upper band, and cellulolytic activity endogenous to Z. mobilis can be seen by the lower band.

Expression of the codon optimized E1 gene sequence was also examined using the promoter, 5' and 3' untranslated regions (UTRs) of the *Z. mobilis* pdc gene, which is a highly transcribed gene with very stable mRNA. This strategy might increase E1 transcription levels and its mRNA stability, thus increasing E1 protein expression. We compared the expression of this new construct with that of the Ptac-driven constructs, and found very low levels of E1 expression using the pdc transcriptional unit (FIG. 4). To ensure that the low levels of E1 expression we witnessed was not a strain-specific phenomena, we examined the expression of all of these different constructs using multiple *Z. mobilis* strains. We found that while both 39676 and ZM4 showed similar expression levels, strain CP4 repeatedly showed a reduced level of expression for all of the constructs suggesting that differences in gene expression can also be strain-specific. We further ruled out the possibility that the E1 protein was being expressed to a high level but was escaping our detection by either being released into the supernatant or forming SDS insoluble aggregates. This was ascertained through immunoblotting of the media supernatant and using Agarose Gel Electrophoresis to Resolve Aggregates (AGERA) techniques, respectively (data not shown).

Figure 5:
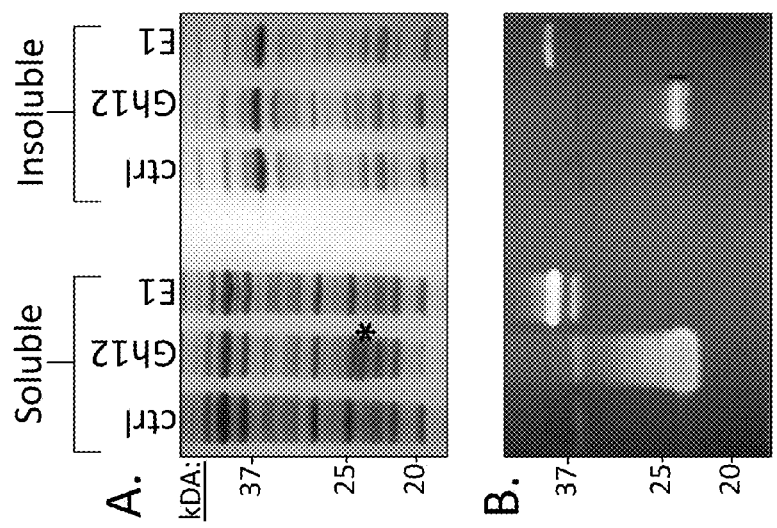
FIG. 5 shows the expression, solubility analysis, and activity of E1 and GH112 in Z. mobilis strain 39676. Protein lysates from Z. mobilis strain 39676 transformed with pZB188 ("control"), p25144 ("GH12"), and p25143 ("E1") were run identically on two independent 12% polyacrylamide gels supplemented with 0.12% carboxymethyl cellulose (CMC). A) Coomassie stain of one of the duplicate polyacrylamide gels shows total protein. The asterisk denotes the location of the GH12 protein. B) A CMC zymogram performed on the second of two duplicate polyacrylamide gels designed to show cellulolytic activity.

We next examined the intracellular expression of GH12 from *A. cellulolyticus* in *Z. mobilis*. Using an identical approach to E1, the GH12 catalytic domain was codon-optimized and subcloned it into a plasmid under control of the tac promoter. The level of GH12 expression observed in *Z. mobilis* stands in contrast to that of E1 as can be seen by SDS-PAGE (FIG. 5A). Specifically, the GH12 protein represented 4.6% (standard deviation: 1.3%; n=6) of the total cellular protein in logarithmically growing cells (as measured by densitometry of Coomassie-stained polyacrylamide gels). Furthermore, nearly all of the GH12 protein expressed in *Z. mobilis* was soluble (FIG. 5A). The protein was enzymatically active as can be seen by CMC degradation using the CMC-zymogram assay (FIG. 5B).

Example 4

We examined the capacity of *Z. mobilis* to secrete both E1 and GH12 extracellularly through the use of predicted secretion signals native to *Z. mobilis*. We chose two independent secretion signals predicted to utilize two separate secretion pathways. The first was that of the phoC gene (ZM0130) predicted to use the SecB-dependent pathway (or Type II secretory pathway), and the second was that from a hypothetical protein (ZM0331) predicted to utilize the Twin Arginine Translocation (TAT) pathway. We initially fused these signals onto the 5' end of the coding sequence of the E1 catalytic domain to create plasmid constructs "Z130-E1" (pJL111) and "Z331-E1" (pJL112).

We next examined the intra-versus extracellular localization of E1 in *Z. mobilis* cultures transformed with either a control vector (pZB188), an intracellularly expressed version of E1 (p25143), or the two E1 constructs tagged with putative secretion signals Z130-E1 (pJL111) and Z331-E1 (pJL112). FIG. 6A shows an amido black stained PVDF membrane showing the total protein found in either the total fraction of a culture ("T", cells plus growth media), or the extracellular fraction ("Ex", the growth media with the cells removed by centrifugation). FIG. 6B shows an anti-E1 immunoblot of the membrane shown in FIG. 6A and shows the localization of E1 in either the total or extracellular fractions. The results show that a significant portion of Z130-E1 and Z331-E1 can be found extracellularly, while E1 without a secretion signal is only found in the total fraction suggesting it is entirely localized intracellularly.

We wanted to ensure that the enzyme found in the extracellular media was in fact due to protein translocation via secretion, and not as a byproduct of passive release due to increased cell death/lysis in the strains with E1 tagged with secretion signals. We first examined the growth media for ADH activity, since ADH is a cytoplasmic protein and should only be found intracellularly. No ADH activity was detected suggesting that there was not a significant increase in cell lysis (data not shown). Secondly, we measured the relative viability of all four cultures using a Live/Dead BacLight bacterial viability kit (Invitrogen). No significant differences in viability were detected among the strains (data not shown). These findings combine to suggest that the E1 protein we detected in the extracellular media was a result of secretion rather than increased levels of cell death in the E1-secreting strains.

Figure 6:
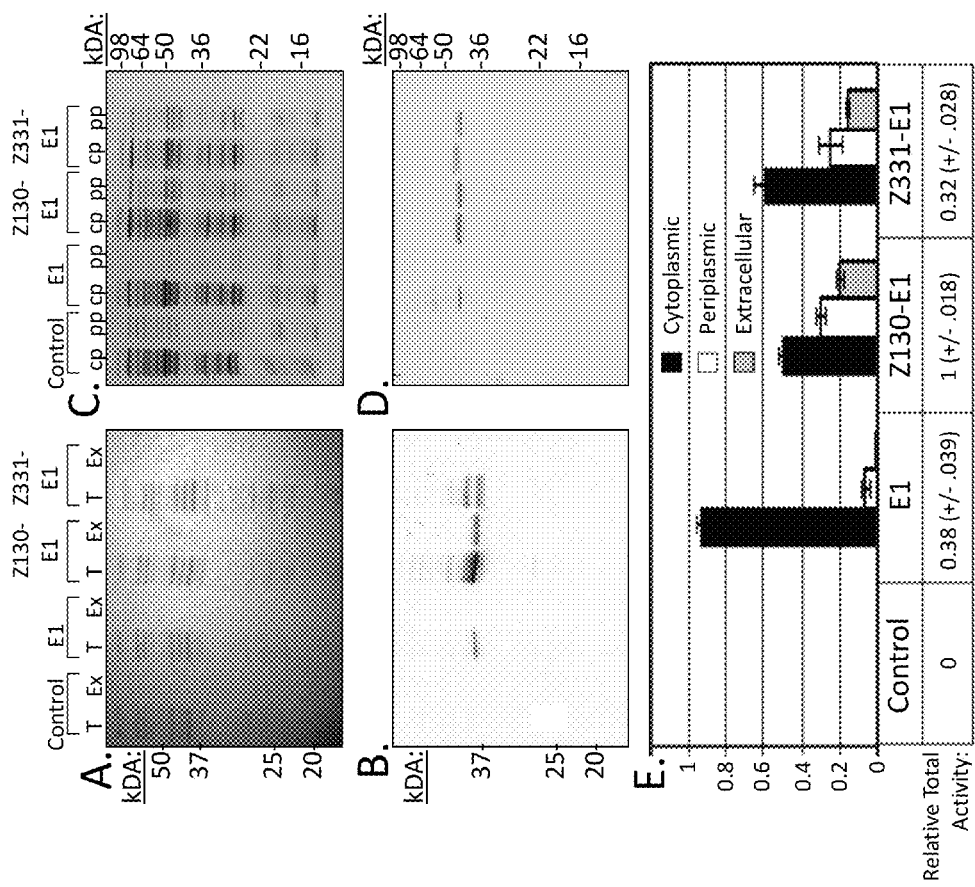
FIG. 6 shows the extracellular secretion and subcellular localization of E1 in Z. mobilis strain 39676. A) Amido black stained PVDF membrane showing Total ("T") and Extracellular Media ("Ex") protein lysate fractions, to show total protein load. B) Anti-E1 immunoblot of the membrane in "A". C) Amido black stained PVDF membrane showing total protein load of protein lysates derived from Z. mobilis expressing multiple versions of E1. The designations "cp" and "pp" represent the cytoplasmic and periplasmic fractions, respectively. D) Anti-E1 immunoblot of the membrane in panel C. E) Relative quantification of E1 activity against methylumbelliferyl cellobiopyranoside in periplasmic, cytoplasmic and extracellular fractions. Relative total activity of equivalent whole cell lysates is shown in the bottom panel.

In Gram-negative bacteria, the SecB-dependent and TAT secretion pathways work in a two-step manner to achieve extracellular secretion (see, e.g., Lee et al., Annu Rev Microbiol 60:373-95). First, proteins are transported across the inner membrane to the periplasm in a signal-dependent manner. Second, the N-terminal signal is removed to form the mature protein, and features of the mature protein dictate its release to the extracellular space. In order to determine how well Z130 and Z331 were functioning to translocate E1 to the periplasmic space, we examined the subcellular localization of the E1 constructs. To achieve this, we isolated periplasmic and cytoplasmic fractions in each of the four strains and examined E1 localization. FIG. 6C shows the amido-black-stained PVDF membrane and represents the total protein load. FIG. 6D shows an anti-E1 immunoblot. These results show that the periplasmic fractions of the strains harboring the E1-secretion plasmids Z130-E1 and Z331-E1 contain more E1 than either the control or the strain harboring the signal-less version of E1, as can be seen by immunoblot and activity (FIGS. 6D and 6E). FIG. 6E shows the relatively quantified cellulolytic activity using the fluorescent substrate 4-methylumbelliferyl β-D-cellobiopyranoside (MUC) in each of the fractions amongst the various strains. The activity of the E1 construct lacking a signal sequence was found almost exclusively in the cytoplasm (94%) while approximately half of Z130-E1 was found either in the periplasmic space (30%) or extracellularly (19%). The activity Z331-E1 was found at a level of 25% in the periplasm and 16% extracellularly. Further, it appears the addition of the Z130 secretion signal increases the overall expression of E1 (FIG. 6).

Figure 7:
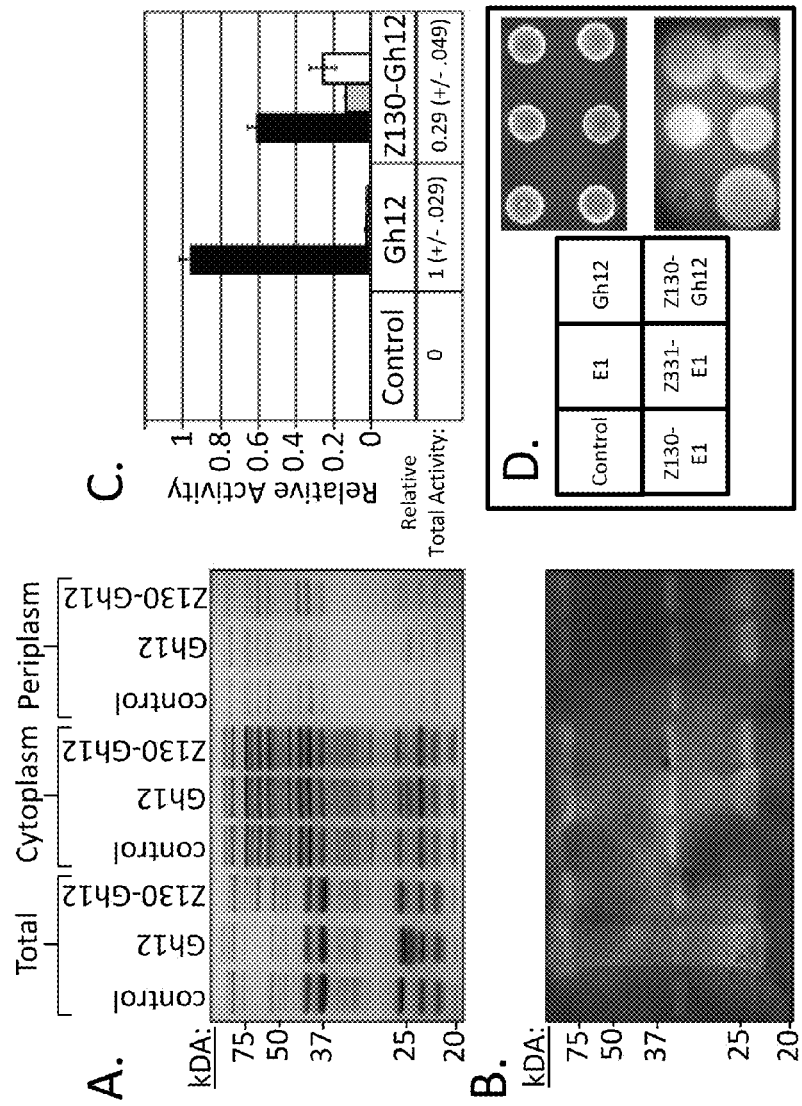
FIG. 7 shows the extracellular secretion and subcellular localization of GH12 in Z. mobilis strain 39676. Whole cell protein lysates, periplasmic and cytoplasmic fractions derived from Z. mobilis strain 39676 transformed with plasmids pZB188 ("control"), p25144 ("GH12") and pJL113 ("Z130-GH12") were run identically on two independent 12% polyacrylamide gels supplemented with 0.12% carboxymethyl cellulose (CMC). A) Coomassie stained gel designed to show total protein. B) A CMC zymogram performed on the second of two duplicate polyacrylamide gels designed to show cellulolytic activity. C) Relative quantification of GH12 activity against methylumbelliferyl cellobiopyranoside in periplasmic, cytoplasmic and extracellular fractions. Relative total activity of equivalent whole cell lysates is shown in the bottom panel. D) Z. mobilis strain 39676 transformed with plasmids pZB188 ("control"), p25143 ("E1"), p25144 ("GH12"), pJL111 ("Z130-E1"), pJL112 ("Z331-E1"), and pJL113 ("Z130-G112") were spotted onto an agar plate containing 2% glucose and 0.12% CMC. After 18 hours of anaerobic growth at 30° C., plates were photographed and cells were washed off. The plate was subsequently stained with 0.2% Congo Red and destained with 1M NaCl and photographed again to show CMC degradation.

We next examined the subcellular localization of GH12 with and without the same Z130 secretion signal used on E1 (FIG. 6). As with E1, the addition of the Z130 secretion signal results in GH12 increasingly localized to the periplasm and extracellular space. This can be seen on coomassie-stained polyacrylamide gel (FIG. 7A) and a corresponding CMC zymogram to show activity (FIG. 7B). FIG. 7C quantifies the subcellular and extracellular activity of GH12 in the three strains as measured by MUC hydrolysis. While the lack of a secretion signal results in 96% of GH12 activity localized within the cytoplasm, the addition of the Z130 signal results in 13% of GH12 activity found in the periplasm and 26% found extracellularly. Again, as was the case for E1-secreting strains (FIG. 6), we were unable to detect ADH activity in the media, and cell viability was indistinguishable between the strains, suggesting that the extracellular pool of GH12 was in fact due to secretion rather than heightened cell lysis. FIG. 7D qualitatively shows the extracellular CMC-degrading activities of all of the strains examined in FIGS. 6 and 7. Culture spots shown in the top panel were washed from the plate which was subsequently stained with Congo red to show CMC degradation.

The Examples discussed above are provided for purposes of illustration and are not intended to be limiting. Still other embodiments and modifications are also contemplated.

While a number of exemplary aspects and embodiments have been discussed above, those of skill in the art will recognize certain modifications, permutations, additions and sub combinations thereof. It is therefore intended that the following appended claims and claims hereafter introduced are interpreted to include all such modifications, permutations, additions and sub-combinations as are within their true spirit and scope.

We claim:

1. A recombinant vector comprising an isolated nucleic acid molecule encoding a polypeptide that functions as a secretion signal in *Zymomonas mobilis*, wherein the polypeptide has an amino acid sequence at least 98% identical to the amino acid sequence of SEQ ID NO:2.

2. The recombinant vector of claim 1, wherein the polypeptide has the amino acid sequence of SEQ ID NO:2.

3. The recombinant vector of claim 1, wherein the nucleic acid molecule has the nucleotide sequence of SEQ ID NO:1.

4. The recombinant vector of claim 1, further comprising a nucleic acid sequence encoding a polypeptide with cellulase activity.

5. The recombinant vector of claim 4, wherein the polypeptide with cellulase activity is an endoglucanase.

6. The recombinant vector of claim 4, wherein the polypeptide with cellulase activity is endoglucanase E1 or endoglucanase GH12 from *Acidothermus cellulolyticus*.

7. The recombinant vector of claim 4, wherein the nucleic acid molecule has the nucleotide sequence of SEQ ID NO:5 or SEQ ID NO:9, or wherein the nucleic acid molecule encodes a polypeptide comprising the amino acid sequence of SEQ ID NO:6 or SEQ ID NO:10.

8. The recombinant vector of claim 1, wherein the recombinant vector is an expression vector.

9. An isolated host cell comprising the recombinant vector of claim 1.

10. The host cell of claim 9, wherein the cell is a microbial cell.

11. The host cell of claim 10, wherein the cell is a *Zymomonas* cell.

12. A method for producing a recombinant polypeptide, comprising:
 a) culturing an isolated host cell comprising the expression vector of claim 8, wherein the host cell expresses a recombinant polypeptide comprising the amino acid sequence of SEQ ID NO:2; and
 b) isolating the recombinant polypeptide.

13. The method of claim 12, wherein the recombinant polypeptide comprises the amino acid sequence of SEQ ID NO:2 fused to a protein with cellulase activity.

14. The method of claim 12, wherein the host cell is a bacterial cell and wherein the recombinant polypeptide is secreted from the host cell and isolated from the cell culture.

15. A method for degrading lignocellulosic biomass, comprising culturing the host cell of claim 9 with the lignocellulosic biomass.

16. The method of claim 12, wherein the host cell is a *Zymomonas* cell.

17. The method of claim 12, wherein the host cell is a *Zymomonas mobilis* cell.

18. The recombinant vector of claim 1, wherein the polypeptide has an amino acid sequence at least 99% identical to the amino acid sequence of SEQ ID NO:2.

* * * * *